(12) United States Patent
Ono et al.

(10) Patent No.: US 8,691,160 B2
(45) Date of Patent: Apr. 8, 2014

(54) SAMPLE ANALYSIS DISC AND METHOD OF PRODUCING SAMPLE ANALYSIS DISC

(75) Inventors: Masayuki Ono, Yokohama (JP); Makoto Itonaga, Yokohama (JP); Koji Tsujita, Yokohama (JP); Yuichi Hasegawa, Yokohama (JP); Kunihisa Matsuzaki, Yokohama (JP)

(73) Assignee: JVC KENWOOD Corporation, Kanagawa-Ku, Yokohama-Shi, Kanagawa-Ken (JP)

( * ) Notice: Subject to any disclaimer, the term of this patent is extended or adjusted under 35 U.S.C. 154(b) by 0 days.

(21) Appl. No.: 13/470,265

(22) Filed: May 12, 2012

(65) Prior Publication Data

US 2012/0288408 A1  Nov. 15, 2012

(30) Foreign Application Priority Data

| May 13, 2011 | (JP) | ................................ | 2011-108255 |
| May 13, 2011 | (JP) | ................................ | 2011-108257 |
| May 13, 2011 | (JP) | ................................ | 2011-108258 |
| Aug. 31, 2011 | (JP) | ................................ | 2011-188549 |
| Dec. 26, 2011 | (JP) | ................................ | 2011-282978 |

(51) Int. Cl.
   *G01N 21/75* (2006.01)
   *G01N 31/22* (2006.01)
   *G01N 33/52* (2006.01)

(52) U.S. Cl.
   USPC ............ 422/402; 422/82.05; 422/62; 422/63; 435/6.1

(58) Field of Classification Search
   USPC ........ 506/39; 435/6.11, 91.1; 422/402, 82.05, 422/62, 63
   See application file for complete search history.

(56) References Cited

U.S. PATENT DOCUMENTS

| 6,342,349 | B1* | 1/2002 | Virtanen ......................... 506/39 |
| 6,812,456 | B2 | 11/2004 | Andersson et al. |
| 7,014,815 | B1 | 3/2006 | Worthington et al. |
| 2007/0054270 | A1 | 3/2007 | Inganas et al. |

FOREIGN PATENT DOCUMENTS

JP            5-5741            1/1993

* cited by examiner

*Primary Examiner* — Sally Merkling
(74) *Attorney, Agent, or Firm* — Renner, Kenner, Greive, Bobak, Taylor & Weber

(57) ABSTRACT

A sample analysis disc has concave sections and convex sections formed alternately in a track area of a disc surface. Labeled beads are immobilized to the track area. Each labeled bead has a biopolymer bound thereto. Only one of the labeled beads is allowed to be filled in each concave section.

16 Claims, 20 Drawing Sheets

| SOLVENT CONCENTRATION | COUNT NUMBER OF LABELED BEADS FOR 100 TRACKS |
|---|---|
| ×100 | 4568210 |
| ×10 | 456790 |
| ×1 | 45688 |
| ×1/10 | 4569 |
| ×1/100 | 456 |
| ×1/1000 | 44 |

FIG. 21

| SOLVENT CONCENTRATION | COUNT NUMBER OF LABELED BEADS FOR 100 TRACKS |
|---|---|
| ×100 | 785536 |
| ×10 | 348651 |
| ×1 | 23560 |
| ×1/10 | 1346 |
| ×1/100 | 53 |
| ×1/1000 | 6 |

FIG. 22

| SOLVENT CONCENTRATION | COUNT NUMBER OF LABELED BEADS FOR 100 TRACKS |
|---|---|
| ×100 | 2924752 |
| ×10 | 348651 |
| ×1 | 20110 |
| ×1/10 | 1824 |
| ×1/100 | 231 |
| ×1/1000 | 10 |

FIG. 23

SAMPLE ANALYSIS DISC AND METHOD OF PRODUCING SAMPLE ANALYSIS DISC

CROSS-REFERENCE TO RELATED APPLICATIONS

This application is based on and claims the benefit of priority from the prior Japanese Patent Applications Nos. 2011-108255 filed on May 13, 2011, 2011-108257 filed on May 13, 2011, 2011-108258 filed on May 13, 2011, 2011-188549 filed on Aug. 31, 2011, and 2011-282978 filed on Dec. 26, 2011, the entire content of which is incorporated herein by reference.

BACKGROUND OF THE INVENTION

The present invention relates to a sample analysis disc for use in sample analysis and a method of producing a sample analysis disc. Especially, this invention relates to a sample analysis disc for use in assay of antigens contained in a biological sample such as blood, biopolymers such as antibodies, etc., and a method of producing a sample analysis disc for use in assay.

Immunoassay for measuring antigens, antibodies, etc. contained a biological sample such as blood has been used widely for the purpose of diagnosis of disease, early diagnosis of disease in a medical checkup. Immunoassay is a method of diagnosing a disease by measuring the concentration of specific antigens (or antibodies) contained in a biological sample. The concentration measurement is performed with quantification of a result of interaction between specific antigens (or antibodies) contained in a biological sample and antibodies (or antigens) conjugated with measurable labels, that can be bound to the specific antigens (or antibodies) in specific binding.

Labels used in immunoassay exhibit high sensitivity and can be treated easily. Therefore, a variety of types of labeling have been developed, for example, RIA (Radio Immunoassay) using radioisotopes, EIA (Enzyme Immunoassay) using enzymes, FIA (Fluorescent Immunoassay) using fluorescent labels, and CLIA (Chemiluminescent Immunoassay) with chemiluminescence.

One type of EIA using enzymes, ELISA (Enzyme-Linked ImmunoSorbent Assay) is popular, especially, using a microplate. This assay is capable of simultaneous measurements of a lot of specimens by an ordinary microplate reader with a 96-well microplate at a relatively low cost. Moreover, ELISA using a microplate is advantageous over RIA using radioisotopes, for less requirements to the environment in which assay is carried out. Nevertheless, ELISA using a microplate is disadvantageous in that the preprocess for immobilizing antibodies to a plate, the antibody-antigen interaction, the B/F (Bond/Free) separation of unreacted labels by washing, the reaction of labels with enzymes, etc. require several ten minutes to several hours, resulting in several hours to about one day in the total assay process.

One tool developed in order to shorten the assay process time is a chip for assay (Lab on a chip) that is a several-centimeter square chip, having a function of assay procedure in each well of a microplate, achieved with device miniaturization technology. The chip is prepared with immobilized antibodies, a specific reagent, etc. on an assay site with ordinary ELISA preprocessing, for shortening the assay process time. Especially, the chip is equipped with a several-ten-micrometer to several-millimeter narrow flow channel that allows the antibody-antigen interaction to occur in a shorter time. Moreover, several chips can be prepared each for dedicated use in one of the assay processes to shorten the total assay process time.

Also developed is the instrument for POCT (Point of Care Test) at or near the site of patient care (in an examination room, at the bedside, etc.). The POCT instrument is useful for particular types of examination such as cardiac marker that require a long time for specimen sampling from a patient up to the result of examination at a clinical laboratory.

SUMMARY OF THE INVENTION

A purpose of the present invention is to provide a sample analysis disc for use in sample analysis and a method of producing a sample analysis disc, capable of measuring antigens, antibodies etc. contained in a sample to be analyzed, at high accuracy.

The present invention provides a sample analysis disc comprising: a disc surface; a track area having concave sections and convex sections formed alternately on the disc surface; and labeled beads immobilized to the track area, each labeled bead having a biopolymer bound thereto, wherein only one of the labeled beads is allowed to be filled in each concave section.

Moreover, the present invention provides a method of producing a sample analysis disc comprising the steps of: forming concave sections and convex sections alternately in a track area of a disc surface; immobilizing labeled beads to the track area, each labeled bead having a biopolymer bound thereto; immobilizing capture biopolymers to the track area, each capture biopolymer to be bound to the biopolymer bound to each labeled bead; and removing specific immobilized capture biopolymers from the track area so that other immobilized capture biopolymers remain immobilized to either the concave or the convex sections.

BRIEF DESCRIPTION OF DRAWINGS

FIG. 21 is view showing a table listing results of counting of labeled beads for an exemplary sample analysis disc produced as explained with reference to FIGS. 9A to 9G;

FIG. 22 is view showing a table listing results of counting of labeled beads for an exemplary sample analysis disc produced as explained with reference to FIGS. 9A to 9G, for comparison; and FIG. 23 is view showing a table listing results of counting of labeled beads for an exemplary sample analysis disc produced as explained with reference to FIGS. 9A to 9G, for comparison.

DETAILED DESCRIPTION OF PREFERRED EMBODIMENTS

Embodiments of a sample analysis disc for use in sample analysis and a method of producing a sample analysis disc according the present invention will be explained with reference to the attached drawings.

Figure 1:
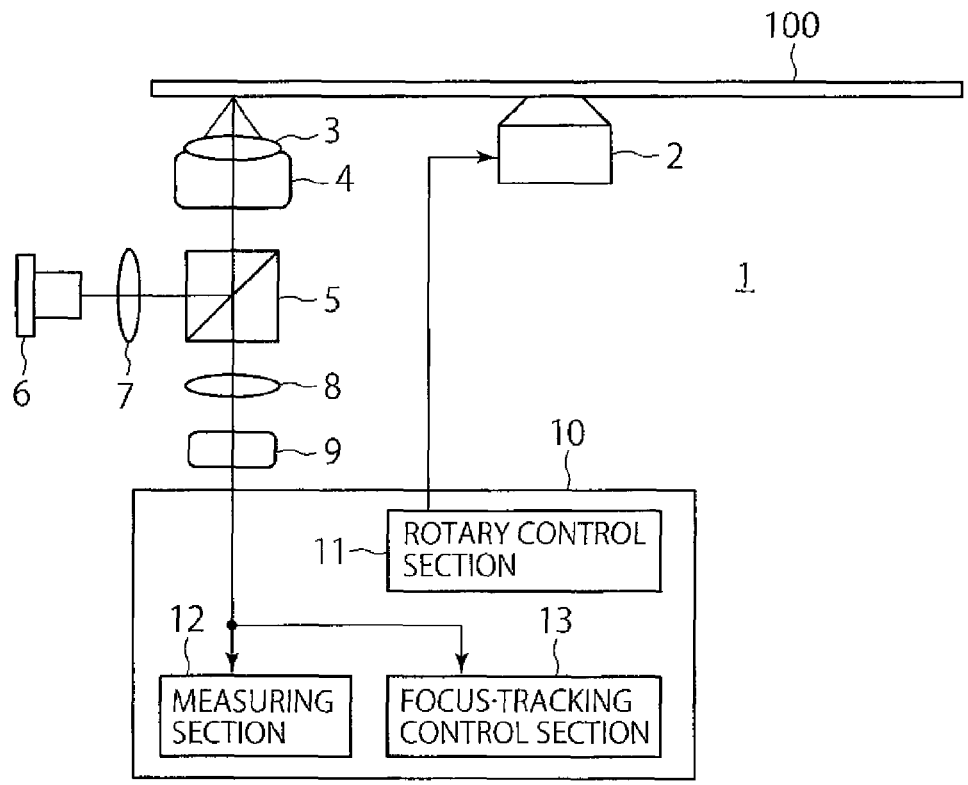
FIG. 1 is a block diagram schematically showing a configuration of a reading apparatus that reads a sample analysis disc according the present invention.

FIG. 1 is a block diagram schematically showing a configuration of a reading apparatus 1 that optically reads a sample analysis disc 100 according the present invention, for use in sample analysis, especially, in measurements of antibodies, antigens, etc.

The reading apparatus 1 is basically the same type as an ordinary reading apparatus that reads data, content, etc. from an optical disc. The reading apparatus 1 is provided with a spindle motor 2, an objective lens 3, an actuator 4, a beam splitter 5, a laser oscillator 6, a collimator lens 7, a condenser lens 8, a photodetector 9, and a controller 10. The reading apparatus 1 can be provided with other elements according to the necessity.

The controller 10 is provided with a rotary control section 11, a measuring section 12, and a focus•tracking control section 13.

The spindle motor 2 rotates the sample analysis disc 100 at a given rotating speed under control by the rotary control section 11. The objective lens 3 has a numerical aperture (NA) of, for example, 0.85 via which a laser beam emitted from the laser oscillator 6 is focused onto a beam spot on the reading surface of the sample analysis disc 100.

The actuator 4 (a two-axis actuator, for example) adjusts the focus of a laser beam emitted from the laser oscillator 6 on the reading surface of the sample analysis disc 100 under control by the focus•tracking control section 13. The beam splitter 5 reflects the laser beam emitted from the laser oscillator 6 towards the objective lens 3 and guides a reflected beam from the sample analysis disc 100 to the photodetector 9.

The laser oscillator 6 is, for example, a semiconductor laser oscillator that emits a laser beam having a wavelength of 405 nm equal to the wavelength used in reproduction of Blu-ray (BD) discs. The laser beam emitted from the laser oscillator 6 is transformed into a collimated beam through the collimator lens 7.

The condenser lens 8 guides the laser beam guided by the beam splitter 5 to the photodetector 9. The photodetector 9 has a quad photodiode that outputs a detection signal (a quad sum signal) corresponding to the amount of light reflected from the sample analysis disc 100 to the measuring section 12 and the focus•tracking control section 13.

The controller 10 is configured, for example, with a CPU (Central Processing Unit), a DSP (Digital Signal Processor), etc., with memories and other necessary elements (not shown). The controller 10 performs a variety of types of control: through operations via an operation section (not shown); based on a detection signal output from the photodetector 9, etc. The variety of types of control include controls by the rotary control section 11, the measuring section 12, and the focus•tracking control section 13, necessary in the present invention. The rotary control section 11, the measuring section 12, and the focus•tracking control section 13 are achieved with specific processes performed by the controller 10, software programs, etc.

The rotary control section 11 controls the spindle motor 2 to rotate the sample analysis disc 100 at a given rotating speed. The measuring section 12 generates an RF signal based on a detection signal output from the photodetector 9. With the RF signal, the measuring section 12 counts the number of labeled beads 110 immobilized to grooves 107 or pits 109 formed on the sample analysis disc 100, which will be described later.

The focus•tracking control section 13 generates several signals, such as, an FE (focus error) signal and a TE (tracking error) signal based on a detection signal output from the photodetector 9. With the generated signals, the focus•tracking control section 13 controls the actuator 4 and other necessary elements for control of the focus of a laser beam on the reading surface of the sample analysis disc 100, tracking, etc.

Figure 2:
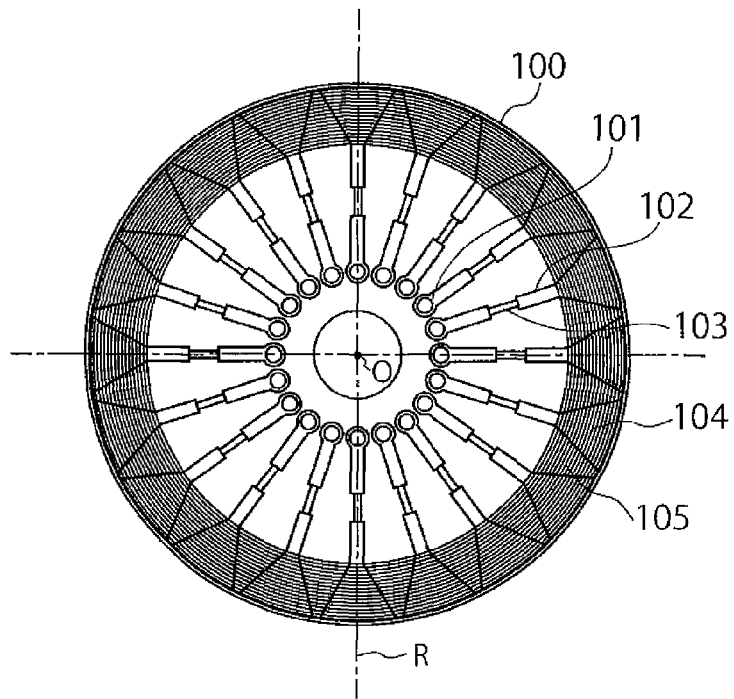
FIG. 2 is a plan view schematically showing a structure of the sample analysis disc according the present invention.

A structure of the sample analysis disc 100 is described with reference to FIGS. 2 to 4. FIG. 2 is a plan view schematically showing a structure of the sample analysis disc 100. The sample analysis disc 100 is formed into a thin flat round shape having the same diameter R as CD (Compact Disc), DVD (Digital Versatile Disc), etc., made of the same material as these media, such as polycarbonate. The sign R (FIG. 2) indicates the diameter or radius of the sample analysis disc 100 in the following description.

As shown in FIG. 2, the sample analysis disc 100 has a plurality of inlets 101 provided in the inner section in rotation symmetry with respect to the center O of the disc 100. Each inlet 101 is an opening through which a sample is dropped, having the capacity suitable for the amount of a sample to be examined.

Connected to the inlets 101 are flow channels 102 formed radially from the center O of the sample analysis disc 100. A sample dropped through an inlet 101 flows through the corresponding flow channel 102. Connected to each flow channel 102 at the outer section of the sample analysis disc 100 is a detection zone 104. Provided at a part of each flow channel 102 is a beads filler 103 in which labeled beads 110 are filled at a predetermined amount. The labeled beads 110 have been modified with antibodies for use in specific binding with particular antigens contained in a sample.

The sample analysis disc 100 may be produced to have the flow channels 102 through processes for MEMS or the like so as to have areas for sample reactions involving antigens, antibodies, labeled beads, etc.

Figure 3A:
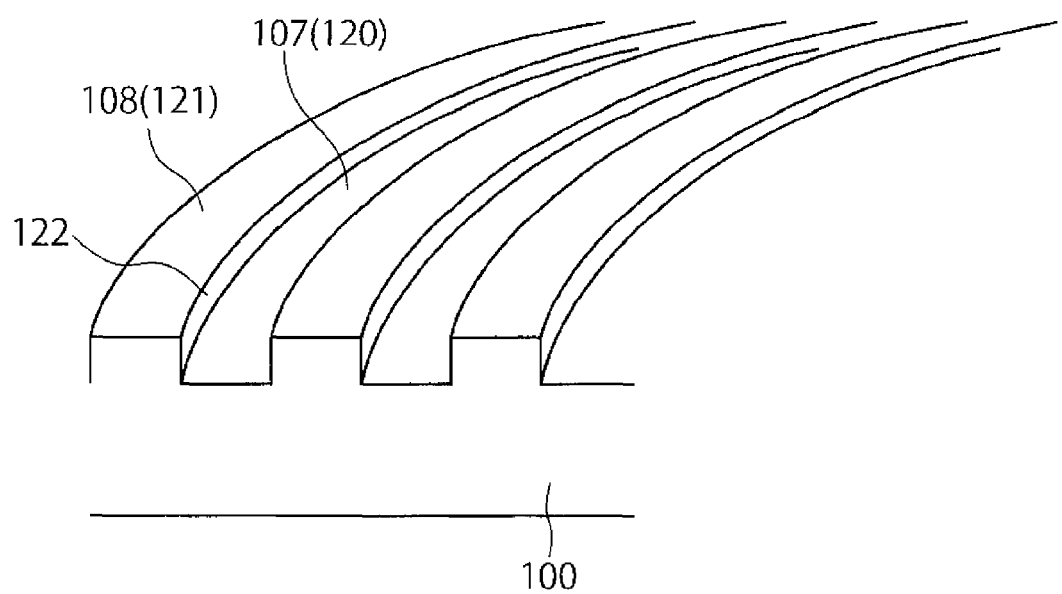
FIG. 3A is a perspective view schematically showing a structure of the sample analysis disc according the present invention.
Figure 3B:
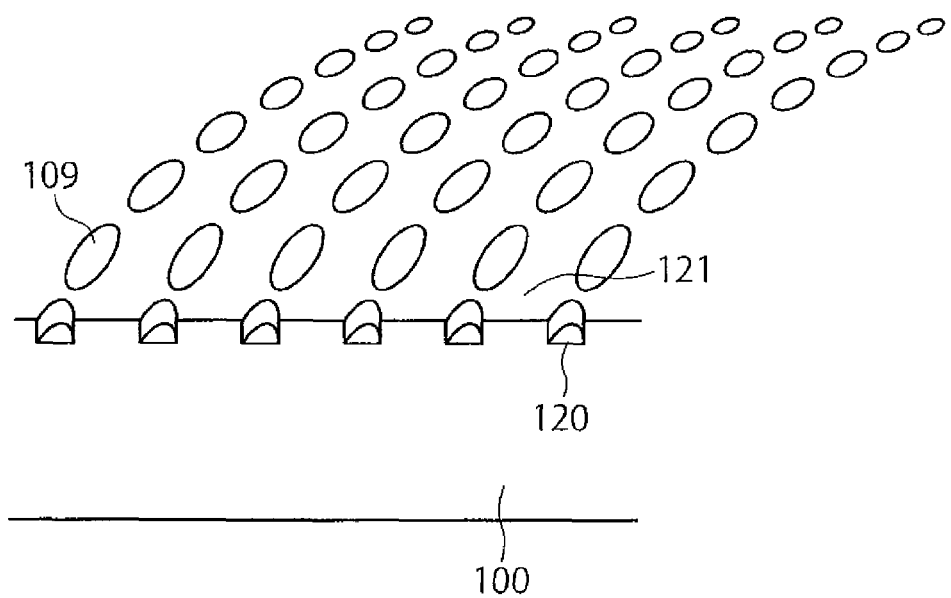
FIG. 3B is a perspective view schematically showing a structure of the sample analysis disc according the present invention.

Also provided at the outer section of the sample analysis disc 100 is a track area 105 that covers the detection zones 104. The track area 105 has grooves 107 (FIG. 3A) or pits 109 (FIG. 3B) provided spirally, like a signal layer of an optical disc. The grooves 107 or pits 109 are formed throughout the track area 105 including the detection zones 104. In the case of grooves, as shown in FIG. 3A, there are grooves 107 and lands 108 on the reading surface of the sample analysis disc 100. In the case of pits, as shown in FIG. 3B, there are pits 109 arranged spirally on the reading surface of the sample analysis disc 100. In FIG. 3A, the grooves 107 and the lands 108 are concave sections 120 and convex sections 121, respectively. Each concave section 120 and a convex section 121 adjacent thereto share a side face 122. In FIG. 3B, the pits 109 are concave sections 120, with convex section 121 for the remaining reading surface of the sample analysis disc 100.

Figure 4:
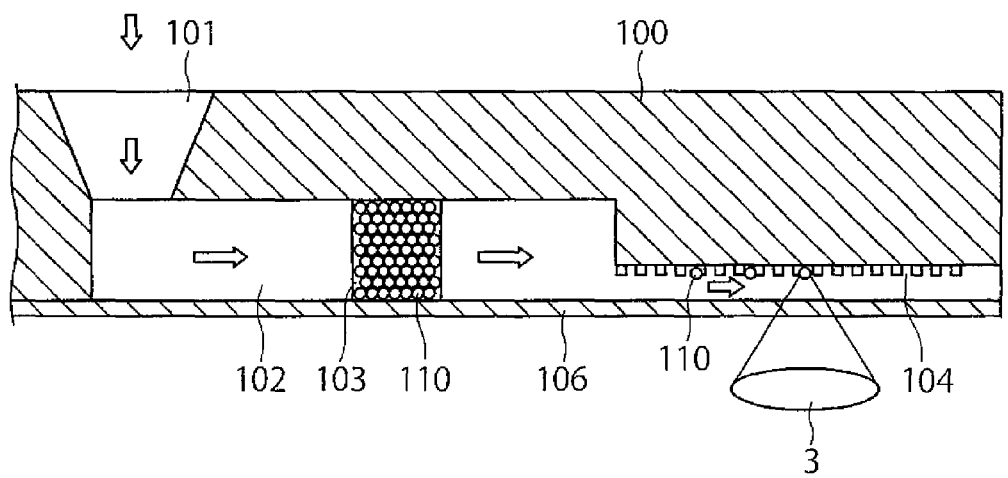
FIG. 4 is a sectional view schematically showing a structure of the sample analysis disc according the present invention, with illustration of beads reading.

FIG. 4 is a sectional view schematically showing a structure of the sample analysis disc 100, with illustration of reading of the labeled beads 110. Provided at the inner section of the sample analysis disc 100 are flow channels 102 with a depth in the range from 100 µm to 500 µm. Formed at a part of each flow channel 102 through which a sample to be analyzed passes is a beads filler 103 in which labeled beads 110 modified with specific antibodies are filled. Formed on the undermost of the sample analysis disc 100 is a protective layer 106.

An antigen-antibody interaction is an interaction between antigens and antibodies in a solution to cause binding of labeled beads 110 and antigens to be analyzed. Generally, antigens to be subjected to immunoassay are contained in a solution at an extremely low concentration. For this reason, the flow channels 102 are formed to have a narrow space so that a lot of labeled beads 110 are filled in a narrow area for higher reaction efficiency of antigens to be analyzed to bind to the labeled beads 110 at a short time.

Labeled beads 110 reacted with a sample in a beads filling filler 103 are transported outwards to a detection zone 104 (as indicated by arrows in FIG. 4) by the centrifugal force caused by the rotation of the sample analysis disc 100 when installed in the reading apparatus 1 shown in FIG. 1. The detection zone 104 is provided with grooves 107 (FIG. 3A) or pits 109 (FIG. 3B), like an ordinary optical disc. In the case of BD, the standards require that data be read from a BD through a 0.1-mm thick protective layer that corresponds to the protective layer 106 shown in FIG. 4. In general, objective lenses (corresponding to the objective lens 3 shown in FIG. 1) of optical pickups for BD are designed to have a working distance of about 0.3 mm to 0.4 mm to the protective layer.

Therefore, under consideration of design margin of the reading apparatus 1, it is preferable for the sample analysis disc 100 to have a narrow space (in the thickness direction) in each detection zone 104 to which the labeled beads 110 reacted with a sample are transported, with respect to the depth of the flow channel 102.

Moreover, the detection zones 104 have to be designed to have a specific area (amount of space) enough for the labeled beads 110 filled in each flow channel 102 not to be piled up one another in the thickness direction so that the beads 110 can be counted one by one. The area of each detection zone 104 is determined so that the grooves 107 or pits 109 have a larger area than an area obtained by multiplying the number of labeled beads 110 filled in each flow channel 102 by the area determined by the diameter of each labeled bead 110. Moreover, the area of each detection zone 104 is determined so that it is larger than the area of the flow channel 102 connected thereto. As shown in FIG. 2, the area of each detection zone 104 becomes wider towards the outer periphery of the sample analysis disc 100. When magnetic beads are used as the labeled beads 110, the beads 110 can react with a sample in a beads filler 103 at a shorter time because of the magnetism that causes forces to pull the beads 110 towards the surface of the grooves 107 or pits 109.

When the sample analysis disc 100 produced having the grooves 107 is installed in the reading apparatus 1 (FIG. 1), a spot beam of a laser beam through the objective lens 3 scans a labeled bead 110 captured in a detection zone 104. Then, a reflected beam from the scanned bead 110 causes a phase shift to change the amount of light to be received by the photodetector 9 that outputs a detection signal. When the labeled beads 110 have a diameter almost equal to the shortest pit length of BD, the labeled beads 110 can be counted one by one in the track area 105.

The location of each labeled bead 110 can be pre-recorded as an address signal in each detection zone 104 having the grooves 107 or pits 109 but not in the section connected to the corresponding flow channel 102 in the sample analysis disc 100. With the address signal, information on the location of a detected labeled bead 110 in the radius and track directions can be obtained.

Information on the location of a detected labeled bead 110 can further be obtained by wobble detection. In wobble detection, an address on the sample analysis disc 100 is calculated from the frequency of a TE signal obtained from the change in undulation of the disc 100 made in the radius direction when the grooves 107 are cut.

Moreover, additional information can be recorded on the signal layer of the sample analysis disc 100 by using a phase-change material or a resin material the same as that used for BD-R, BD-RW, etc. For example, an ID number of a sample dropped in the sample analysis disc 100 is recorded before the disc 100 is detached from the reading apparatus 1. The ID number is used for identifying the sample already analyzed, in the next sample analysis. It is also possible to avoid a mistake of dropping of a new sample in the analysis area of the sample analysis disc 100 already used in the former sample analysis.

The analysis of a sample using the sample analysis disc 100 according to the present invention will be described with reference to FIGS. 5A to 8B.

A sample to be analyzed is dropped (injected) into the sample analysis disc 100 through an inlet 101 (FIG. 2). Then, the sample analysis disc 100 is installed in the reading apparatus 1 as shown in FIG. 1. The sample analysis disc 100 is rotated so that the dropped sample is transported to the flow channel 102 connected to the inlet 101 by the centrifugal force, for causing the antigen-antibody interaction. The beads filler 103 provided at a part of the flow channel 102 has been filled with labeled beads 110 modified with antibodies for use in specific binding with particular antigens contained in the sample to be analyzed.

The materials that can be used as the labeled beads 110 are polymer particles each having a diameter of about 100 nm to 1 μm, magnetic beads containing a magnetic material such as ferrite, metal nanoparticles such as colloidal gold, silica beads, etc. The diameter of the labeled beads 110 depends on the optical system or mechanism to be used in measurements (analysis). Therefore, the most appropriate diameter is decided according to the type of optical system or mechanism to be used. The optical resolution limit d is given by the following expression (1):

$$d = 0.25 \times \lambda / NA \qquad (1)$$

where $\lambda$ is a wavelength of a laser beam and NA is a numerical aperture of an objective lens.

Among the optical discs currently available on the market, Blu-ray Disc (BD) exhibits the highest resolution that allows a spot of a laser beam having a wavelength of 405 nm from a semiconductor laser to be focused on the disc thorough an objective lens having a numerical aperture (NA) of 0.85. The shortest pit length for signals to be recorded on BDs is about 150 nm. Therefore, although not limited to the optical system (mechanism) for BDs, when the optical system for BDs is used for the reading apparatus 1, labeled beads having a size up to about 120 nm in diameter can be detected according to the expression (1).

Accordingly, the present invention is advantageous in that the reading apparatus 1 can be produced as an analyzer with parts that are used for drive mechanisms for ordinary optical discs, especially optical pickups, at a very low cost but exhibiting accuracy as high as or higher than current expensive analyzers, for biopolymer measurements (detection).

A pre-process is performed to the labeled beads 110 to bind an antibody 210 to the surface of each labeled bead 110. The antibody 210 is the one to bind in specific binding to an antigen 200 contained in a sample. There are a variety of types for the antibody 210. One type is HBsAg monoclonal antibody that binds to HBs antigen contained in blood in specific binding. For examination of hepatitis B, the labeled beads 110 are modified with HBsAg monoclonal antibodies, beforehand. The type of the antibody 210 to be selected depends on the type of the antigen 200 to be measured and to which the antibody 210 binds in specific binding.

When a sample is mixed with each labeled bead 110 modified with an antibody 210 in a flow channel 102, an antigen 200 contained in the sample binds in specific binding to the antibody 210 that has bounded to the surface of the labeled bead 110. Formed in a solution through the specific binding is a compound of the labeled bead 110, the antibody 210, and the antigen 200.

Existing in the solution at this stage are the labeled beads 110 of the compounds formed by the interaction between the antigens 200 and the antibodies 210, and also other labeled beads 110 for which no antibody-antibody interaction occurred. The labeled beads 110 of the compounds and the other labeled beads 110 exist at a specific ratio depending on the amount of the antigens 200 contained in the sample. The solution that contains the compounds formed by the interaction is then transported to the detection zone 104 at the outer side of the sample analysis disc 100 by the centrifugal force generated by the rotation of the disc 100.

The detection zone 104 has the grooves 107 or pits 109 arranged spirally on its surface that is connected to the upper surface of the flow channel 102, as shown in FIG. 4, like the signal layer of optical discs, as described above. It is preferable that the width of each groove 107 or pit 109 is almost equal to the diameter of the labeled beads 110 to be used as a label.

If the diameter of the labeled beads 110 is small, for example, less than half the width of the grooves 107 or pits 109, a plurality of labeled beads 110 stick together in the grooves 107 or pits 109 and are immobilized there, resulting in difficulty in analyzing a sample accurately. For this reason, it is preferable that the width of the grooves 107 or pits 109 is almost equal to or smaller than the diameter of the labeled beads 110. Especially, in order to avoid immobilization of two or more of labeled beads 110, it is required that the size (diameter) of each labeled bead 110 be at least half the width of the grooves 107 or pits 109. The diameter of labeled beads 110 can be adjusted by a known technique.

Concerning the diameter of labeled bead 110 and the width of the grooves 107 or pits 109, it is preferable that a ratio D/W satisfies the following expression (2):

$$0.6 \leq D/W < 1.0 \quad (2)$$

where D is the diameter of each labeled bead 110 and W is the width of each of the grooves 107 or pits 109 that form a fine concave-convex alternate structure on the substrate surface of the sample analysis disc 100.

If the diameter of each labeled bead 110 is larger than the width of each groove 107 or pit 109, the labeled bead 110 cannot be filled in the groove 107 or pit 109 completely. This incomplete filling causes the instability of a tracking signal, crosstalk between adjacent tracks of the sample analysis disc 100, etc. that affect the quantitativity of a sample.

Moreover, if a sample is merely dropped into the sample analysis disc 100 with a tool, such as a pipette, a labeled bead 110 is immobilized not only to a groove 107 but also a land 108. The same problem also occurs for the pits 109. This unnecessary immobilization generates crosstalk components that cause inaccurate measurements. Therefore, it is required that the width ratio of the lands 108 to grooves 107 or the width of the pits 109 be determined appropriately so that a labeled bead 110 can be immobilized only to a groove 107 or pit 109.

Generally, it is preferable to set the land-to-groove ratio (a width ratio of the lands 108 to grooves 107) to about 0.5 to obtain a stable TE (tracking error) signal. Nevertheless, it is preferable for the land-to-groove ratio to be as high as possible unless the TE signal becomes unstable. It is preferable that a ratio W/I satisfies the following expression (3):

$$0.65 \leq W/I \quad (3)$$

where W is the width of each of the grooves 107 or pits 109 that form a fine concave-convex alternate structure on the substrate surface of the sample analysis disc 100 and I is the interval between adjacent two grooves 107 or pits 109. The interval is defined as follows. In FIG. 3A, each groove 107 has a first left edge section and an opposite second right edge section that is closer than the first edge section to the center O (FIG. 2) of the sample analysis disc 100 in the direction of the radius R (in FIG. 2). The interval is the distance between the first (or the second) edge section of each groove 107 and the first (or the second) edge section of a groove 107 next to the each groove 107. The same definition is applied to the pits 109.

The depth of each groove 107 or pit 109 is set to a value (generally, about λ/8) to give an appropriate TE-signal level. It is, however, not always necessary to set the depth to the value mentioned above. This is because the TE-signal level depends on several factors such as the relationship between the size of the labeled beads 110 and the output (detection) signals and how the detection signals are distinguishable from other signals caused by scratches, dust, etc. on the sample analysis disc 100.

In the detection zone 104 having the grooves 107 or pits 109, antibodies 210 the same type as those bounded to the surface of the labeled beads 110 are immobilized by silane coupling, for example. The antigens 200 contained in the solution transported to the detection zone 104 further interact with the antibodies 210 immobilized in the detection zone 104. Precisely, the substances that undergo the further interaction are the compounds formed by the interaction between the antigens 200 and the antibodies 210 that have modified the labeled beads 110 in the flow channel 102. The further interaction forms sandwich compounds each having a labeled bead 110, an antibody 210 that has modified the labeled bead 110, an antigen 200, and an antibody 210 immobilized in the detection zone 104, as an immobilized antibody. The sandwich compounds are then immobilized in the detection zone 104 of the sample analysis disc 100. The labeled beads 110 for which the antibodies 210 have not interacted with the antigens 200 are transported further to the outer side of the sample analysis disc 100 by the centrifugal force. The labeled beads 110 for which no interaction occurred are then discharged from the detection zone 104 to the outside.

It is possible to form the labeled beads 110 containing a magnetic material, such as ferrite, so that magnetic manipulation of the beads 110 can be performed within the sample analysis disc 100 or externally. The magnetic manipulation serves to raise a reaction rate of the labeled beads 110 immobilized only to the grooves 107, detection accuracy, etc.

Figure 5A:
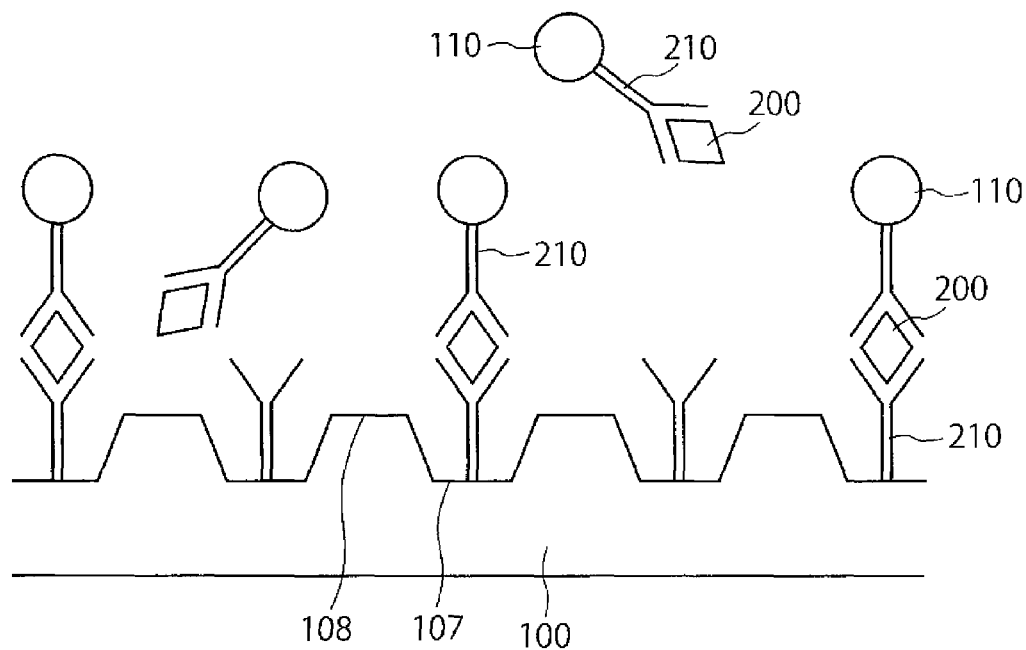
FIG. 5A is a view schematically illustrating the reaction of a sample on the sample analysis disc according the present invention.
Figure 5B:
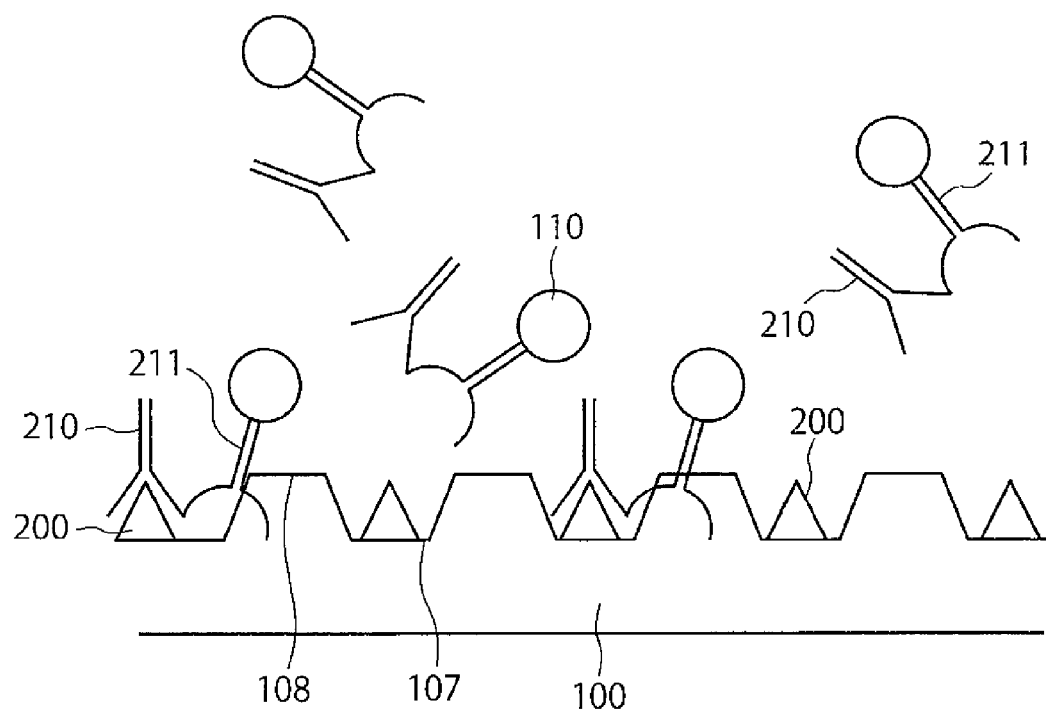
FIG. 5B is a view schematically illustrating the reaction of a sample on the sample analysis disc according the present invention.

FIGS. 5A and 5B are views schematically illustrating the reaction of a sample, with illustration of a structure of the compounds formed after the interaction between the antigen 200 and the antibody 210 on the sample analysis disc 100.

FIG. 5A shows the immobilization of the compounds in the detection zone 104, with the labeled beads 110 (measurable labels) bounded to the antigens 200 contained in a sample, according to the principle of a sandwich assay in the same way as using a well plate. The sandwich assay is a popular method of quantification to obtain a linear output in relation to the absolute amount of a target to be detected. The immobilization can be done by another method such as a competition method.

When the target to be detected is not the antigens 200 but the antibodies 210, as shown in FIG. 5B, antigens 200 for use in specific binding with the antibodies 210 are immobilized in the detection zone 104 and then the labeled beads 110 are bounded to the antibodies 210 with secondary antibodies 211. These procedures allow a sandwich assay of the antibodies 210, in the same way as for the antigens 200.

Explained next with reference to FIGS. 6A to 6E (schematic illustrations) is an ordinary sample analysis method using the sample analysis disc 100 according to the present invention.

Figure 6A:
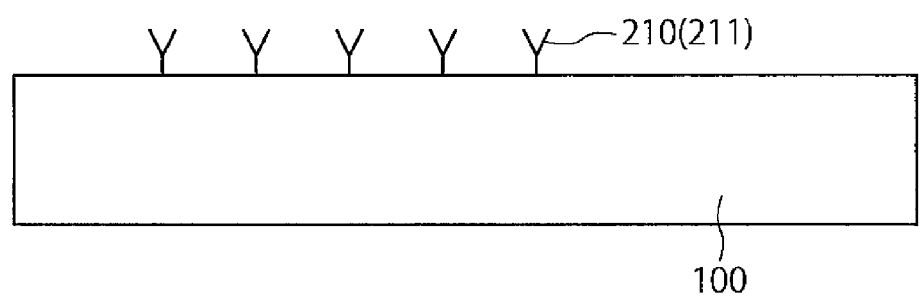
FIG. 6A is a view schematically illustrating an ordinary sample analysis method using the sample analysis disc according to the present invention.

Firstly, as shown in FIG. 6A, antibodies 210 are immobilized on the sample analysis disc 100. The antibodies 210 are used in specific interaction with antigens 200 (not shown) that are biopolymers to be captured for quantitative analysis. The antibodies 210 are referred to as capture antibodies 211 (capture biopolymers), hereinafter, for capturing the target antigens 200.

Figure 6B:
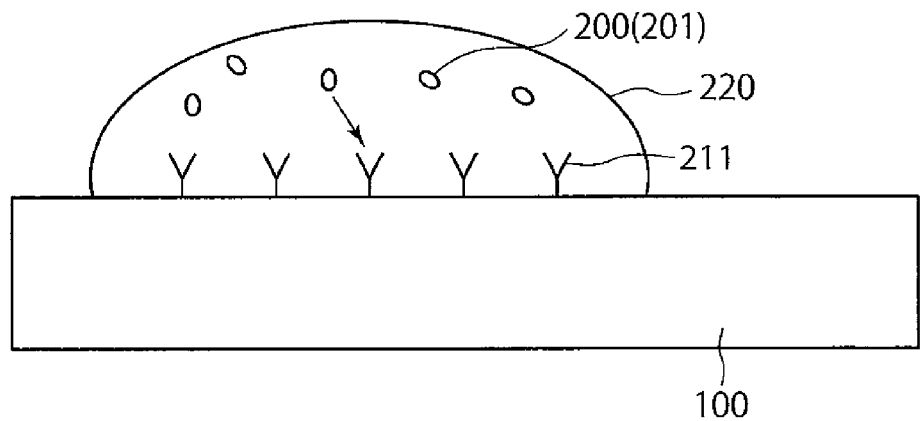
FIG. 6B is a view schematically illustrating an ordinary sample analysis method using the sample analysis disc according to the present invention.

Next, as shown in FIG. 6B, a sample solution 220, such as a body fluid, is dropped onto the sample analysis disc 100 to cause an antigen-antibody interaction between antigens 200 to be captured (contained in the sample solution 220) and the capture antibodies 211. The antigen-antibody interaction allows the capture antibodies 211 to capture the antigens 200.

The captured antigens 200 are referred to as antigens 201 for assay (biopolymers for assay).

Figure 6C:
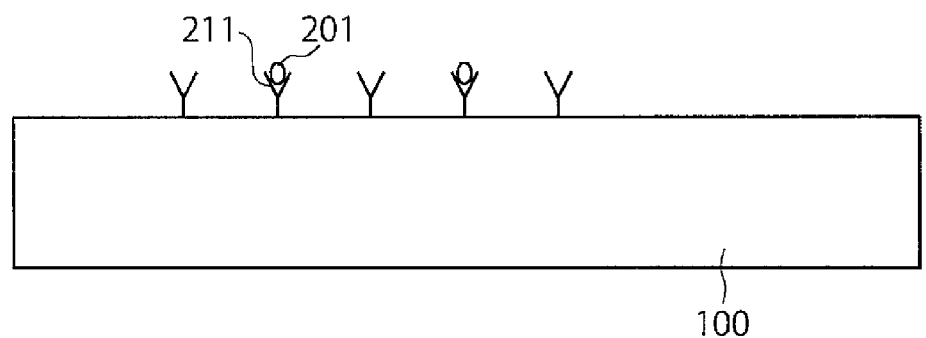
FIG. 6C is a view schematically illustrating an ordinary sample analysis method using the sample analysis disc according to the present invention.

Next, as shown in FIG. 6C, the sample solution 220 dropped onto the sample analysis disc 100 is washed by spin washing with pure water or the like to wash away the antibodies 210 that have not captured the antigens 200. Those remaining on the sample analysis disc 100 after the spin washing are the capture antibodies 211 and the antigens 201 for assay captured by the capture antibodies 211.

Figure 6D:
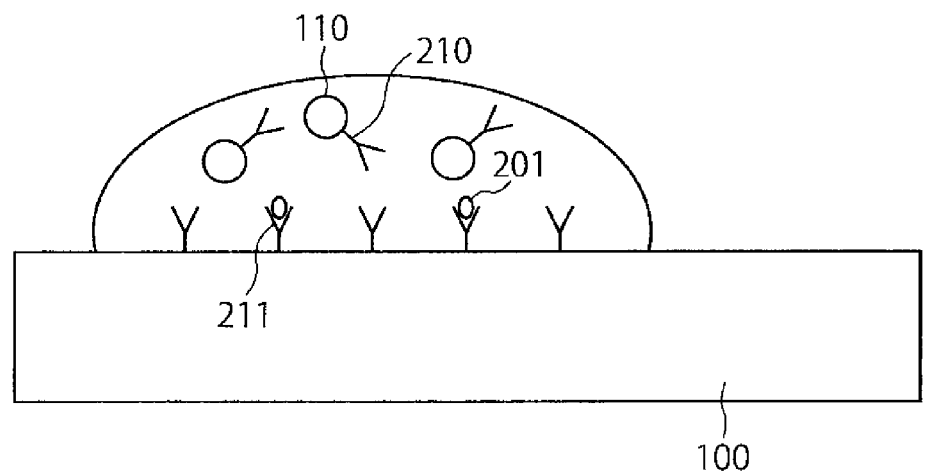
FIG. 6D is a view schematically illustrating an ordinary sample analysis method using the sample analysis disc according to the present invention.

Next, as shown in FIG. 6D, a solution containing dispersed antibodies 210 to which labeled beads 110 have bound is dropped onto the sample analysis disc 100 to cause an antigen-antibody interaction between the antibodies 210 and the antigens 201 for assay captured by the capture antibodies 211.

Figure 6E:
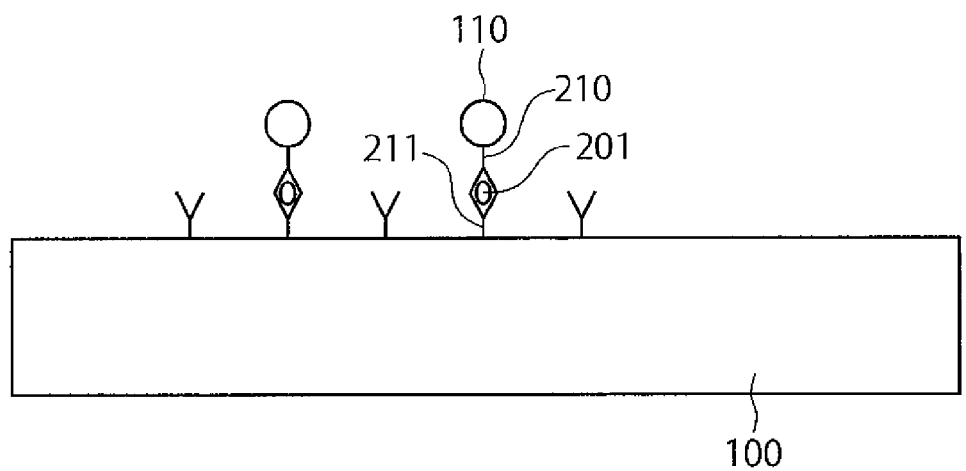
FIG. 6E is a view schematically illustrating an ordinary sample analysis method using the sample analysis disc according to the present invention.

Next, as shown in FIG. 6E, the sample analysis disc 100 is washed by spin washing with pure water or the like to wash away the antibodies 210 to which the labeled beads 110 have bound but which have not interacted with the antigens 201 for assay captured by the capture antibodies 211. In this way, the antigens 201 for assay that are sandwiched by the antibodies 210 to which the labeled beads 110 have bound and the capture antibodies 211 are only immobilized on the sample analysis disc 100. Then, the sample analysis disc 100 having the antigens 201 for assay immobilized thereon is installed in the reading apparatus 1, as shown in FIG. 1.

Figure 6F:
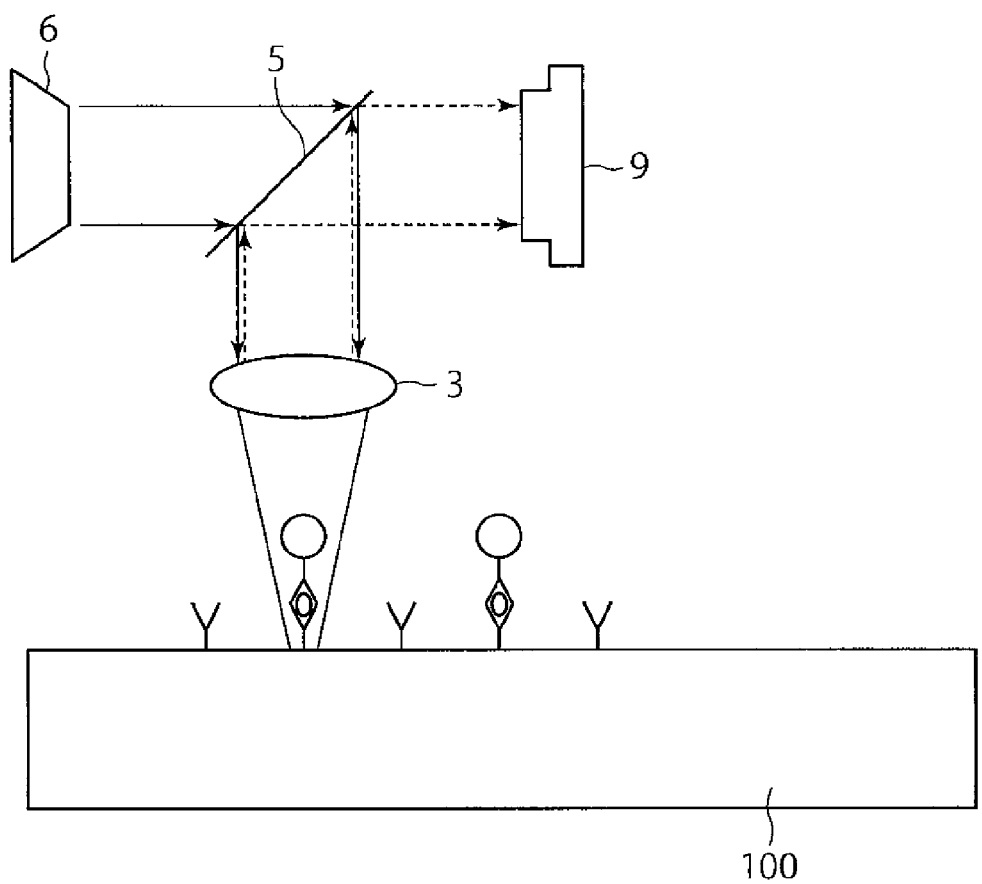
FIG. 6F is a view schematically illustrating an ordinary sample analysis method using the sample analysis disc according to the present invention.

Next, as shown in FIG. 6F, the sample analysis disc 100 is exposed to a beam spot while being rotated by the spindle motor 2, the beam spot being formed by the focus of a laser beam emitted from the laser oscillator 6 through the objective lens 3. Under tracking control by the focus tracking control section 13, the photodetector 9 receives a reflected laser beam from the sample analysis disc 100. The amount of light of the reflected beam depends on whether there is a labeled bead 110 bound to an antibody 210 that has sandwiched an antigen 201 for assay with a capture antibody 211. Then, the photodetector 9 outputs a detection signal corresponding to the amount of light of the reflected beam to the measuring section and the focus tracking control section 13. Then, the measuring section 12 counts the number of the labeled beads 110 (precisely, the number of biopolymers) based on a waveform of the detection signal.

The capture antibodies 211 explained with reference to FIG. 6A can be obtained and immobilized on the sample analysis disc 100, as follows. Capture antibodies are dispersed in a buffer solution adjusted to have a pH-value suitable for the capture antibodies to be immobilized. The buffer solution is then dropped onto or applied on the sample analysis disc 100 and spread over a part of the surface or the entire surface of the sample analysis disc 100. The sample analysis disc 100 having the buffer solution thereon is then left for a specific time at an appropriate temperature. Accordingly, the capture antibodies dispersed in the buffer solution are physically adhered or chemically bound to the sample analysis disc 100 to become the capture antibodies 211 explained above.

The sample analysis disc 100 according to the present invention will be explained in more detail. Explained below is the sample analysis disc 100 having a land-groove alternate structure. However, not only a disc having a land-groove alternate structure, the present invention is applicable to a ROM-type disc having a train of continuous pits with a minute concave-convex alternate structure, the centers of continuous pits being subjected to tracking, a disc having a combination of the land-groove alternate structure and the train of continuous pits, etc.

The radiation of a laser beam to the sample analysis disc 100 in the reading apparatus 1 is performed to the front disc surface having the lands 108 and grooves 107 (FIG. 3A) or the pits 109 (FIG. 3B). However, it can be performed to the rear disc surface when the substrate of the sample analysis disc 100 is made of a material that allows a laser beam to pass therethrough.

Figure 7:
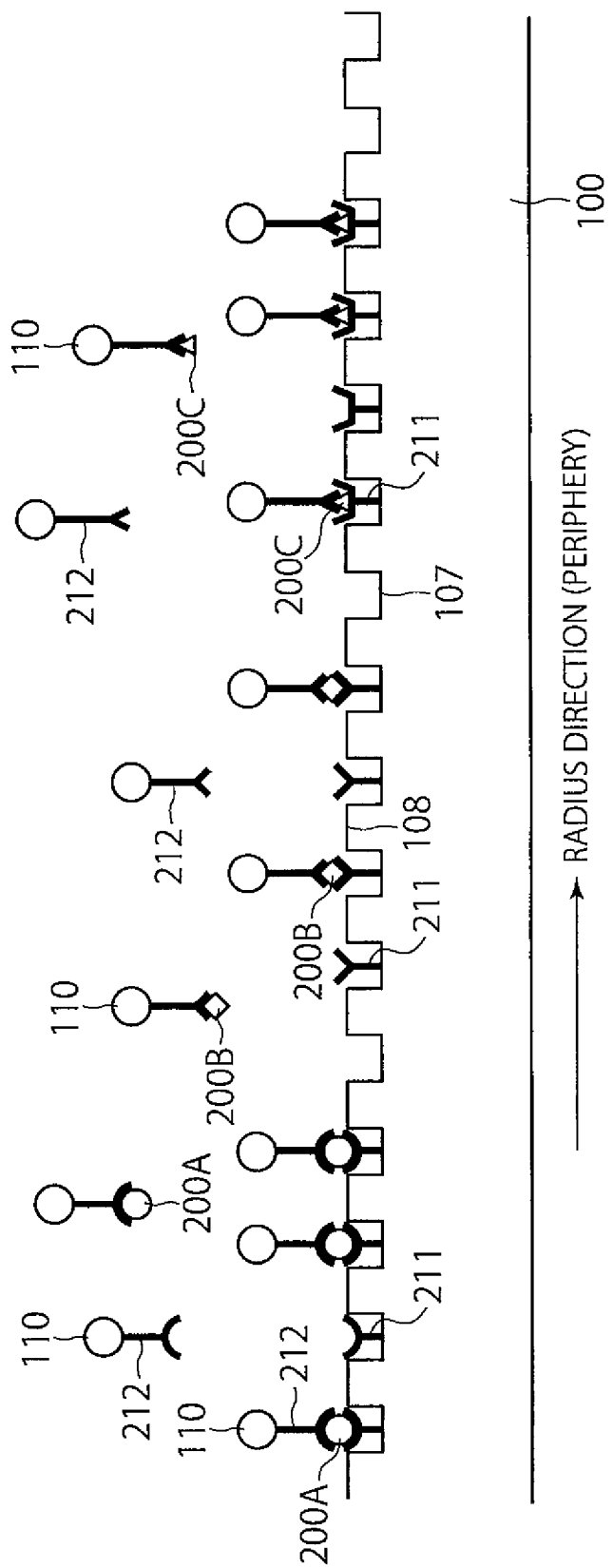
FIG. 7 is a view schematically illustrating the reaction of a sample on the sample analysis disc according the present invention.

FIG. 7 is a sectional view of the sample analysis disc 100, schematically illustrating the detection zone 104 in which a plurality of antibodies are immobilized in the radius direction of the sample analysis disc 100. In FIG. 7, monoclonal antibodies (capture antibodies 211) to be bound in specific binding to a plurality of antigens 200A to 200C in a sample to be analyzed are immobilized to the tracks (a plurality of separate zones) of the sample analysis disc 100. Labeled beads 110 are modified with polyclonal antibodies 212 to be bound to antigens. The polyclonal antibodies 212 of the labeled beads 110 dispersed over the detection zone 104 interact with different types of antigens 200A to 200C according to the positions on the disc radius (the distance from the center O of the sample analysis disc 100 in FIG. 2) and then bind to the grooves 107 (or pits 109 if formed instead of the grooves 107).

Generally, simultaneous detection of a plurality of antigens through fluorescence or enzyme reaction is performed based on the difference in fluorescence emission wavelength or coloring from a plurality of labels. The simultaneous detection of antigens through fluorescence or enzyme reaction, however, requires light sources or wave filters for different wavelengths and a photodetector for each wavelength.

Different from the detection of antigens through fluorescence or enzyme reaction, in the present invention, the location of each labeled bead 110 in the radius direction of the sample analysis disc 100 can be recorded beforehand as an address signal in each detection zone 104 having the grooves 107 (or pits 109), as already described. Therefore, in FIG. 7, a plurality of antigens can be simultaneously detected with address signals. This scheme can also be applied to an assay for statistically determining the possibility of a disease based on an antigen content ratio. In the statistical determination, the scheme allows the same sample to be analyzed in the same conditions with fewer variations in the result of analysis than analysis in different conditions.

Figure 8A:
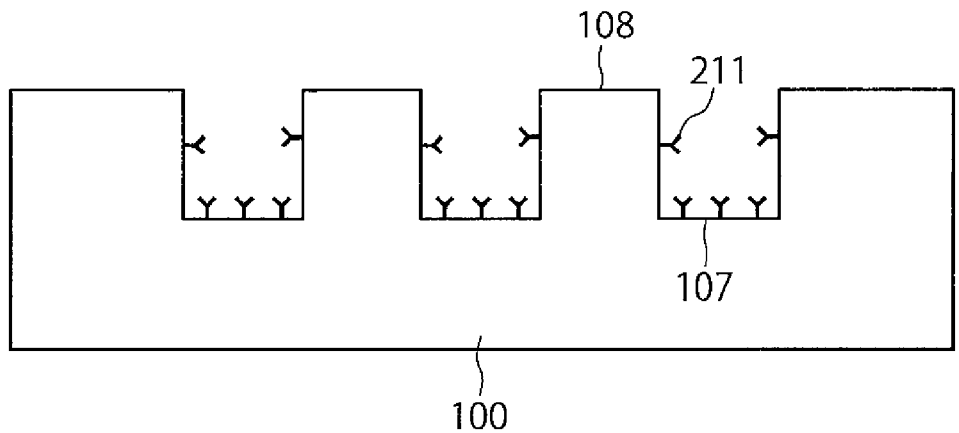
FIG. 8A is a sectional view schematically illustrating the sample analysis disc 100 according to the present invention.
Figure 8B:
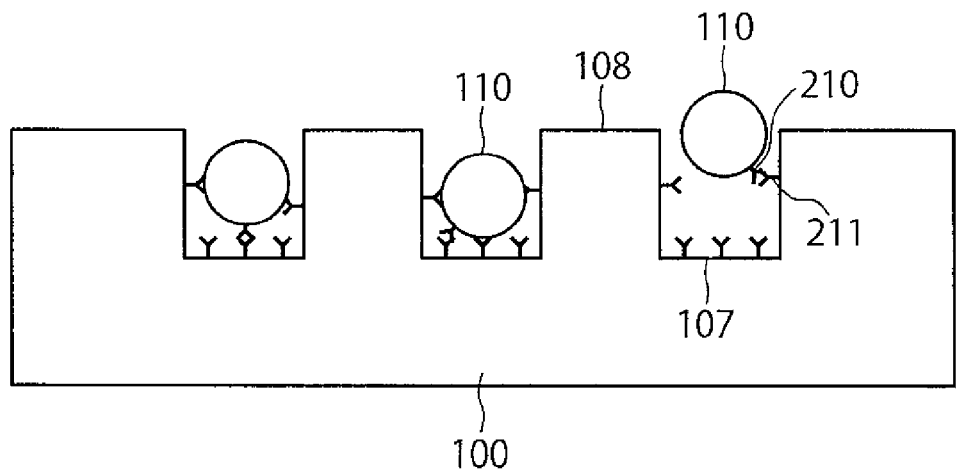
FIG. 8B is a sectional view schematically illustrating the sample analysis disc 100 according to the present invention.

FIGS. 8A and 8B are sectional views schematically illustrating the sample analysis disc 100 formed into an optical disc-like biochip, according to the present invention.

FIG. 8A shows that capture antibodies 211 are immobilized only on the bottom and side wall of each groove 107 of the sample analysis disc 100, not on the lands 108. The immobilization of the capture antibodies 211 only to the grooves 107 allows antibodies 210 (the capture antibodies 211) having labeled beads 110 bound thereto and also antigens 201 for assay (not shown) bound thereto in the later procedure to be immobilized to the grooves 107 only, as shown in FIG. 8B. The immobilization only to the grooves 107 is achieved by setting the width ratio of the lands 108 to the grooves 107 to a specific value so that a labeled bead 110 can be immobilized only to a groove 107, without being immobilized to a land 108, as already explained.

Different from the sample analysis disc 100 shown in FIG. 8A, in a known biochip formed like an optical disc, capture antibodies are immobilized to both of grooves and lands. In the known biochip, antibodies (capture antibodies) having labeled beads bound thereto and also antigens for assay bound thereto in the later procedure are immobilized to both of the grooves and lands. Therefore, if this antibody-immobilized known biochip is installed in the reading apparatus 1 shown in FIG. 1, tracking of the grooves causes interference of the labeled bead immobilized to the land next to the groove now under tracking. The interference causes change in waveform of signals detected from the known biochip, which could result in erroneous counting of the labeled beads immobilized to the lands as those immobilized to the grooves. In detail, the labeled beads counted while the lands are being traced could also be counted while the grooves are being traced. If this happens, the same labeled bead is counted twice, which results in count error in which the count number of antigens for assay becomes larger than the actual number.

On the other hand, in the sample analysis disc 100 of the present invention, the antibodies 210 (the capture antibodies 211) having the labeled beads 110 bound thereto and the antigens 201 for assay bound thereto are immobilized to the grooves 107 only, as explained with respect to FIGS. 8A and 8B. The immobilization of the antibodies 210 (the capture antibodies 211) only to the grooves 107 allows the counting of the labeled beads 110 at high quantitativity. The immobilization of the antibodies 210 (the capture antibodies 211) only to the lands 108 can also be done in the same way, which can further be done to the pits 109 when the sample analysis disc 100 is produced with the pits 109 instead of the grooves 107 and lands 108. These modification also achieve the counting of the labeled beads 110 at high quantitativity.

Described next a method of producing the sample analysis disc 100 according to the present invention with reference to FIGS. 9A to 9G and FIGS. 20A to 20G. The sample analysis disc 100 according to the present invention is produced in a similar manner as CDs, DVDs, etc. except for the flow channels 102 and beads fillers 103 (FIG. 4). The flow channels 102 and beads fillers 103 are not unique features of the present invention and can be formed by a known technique, hence the formation of the flow channels 102 and beads fillers 103 is omitted from the following description. Between FIGS. 9A to 9G and FIGS. 20A to 20G, the basic processes are the same, except for the concave sections 120 and convex sections 121 (FIG. 3A) to have different surface roughness by different etching processes, which will be described later. Therefore, basically the same explanation is used for FIGS. 9A to 9G and FIGS. 20A to 20G, even though the illustrations are little bit different from each other.

Figure 9A:
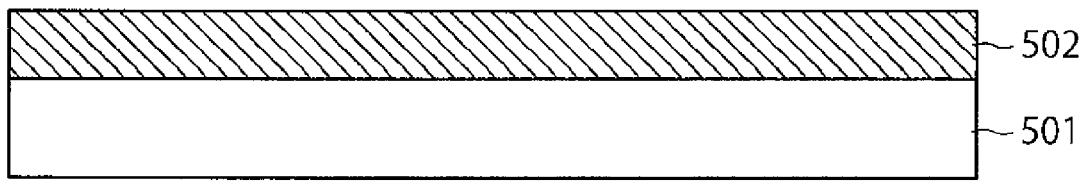
FIG. 9A is a sectional view schematically illustrating a method of producing the sample analysis disc according to the present invention.
Figure 20A:
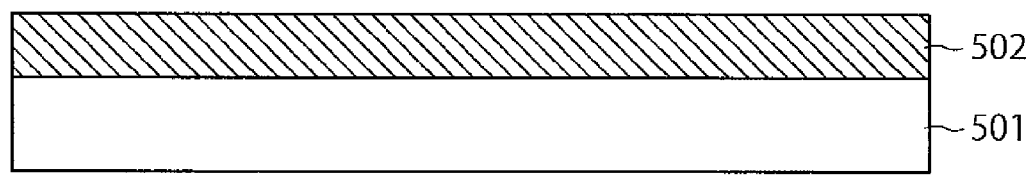
FIG. 20A is a sectional view schematically illustrating a method of producing the sample analysis disc according to the present invention.

Firstly, as shown in FIGS. 9A and 20A, a disc substrate 501 is prepared with optical polishing and washing, followed by drying for a sufficient time. Sputtering, such as magnetron sputtering, is performed to the disc substrate 501 to form an inorganic resist film 502 thereon with a film thickness in the range from about 10 nm to 100 nm. The substrate 501 may be a quarts glass substrate or a silicon wafer substrate. The silicon wafer substrate is more suitable as the substrate 501 than the quarts glass substrate. This is because, the silicon wafer substrate is used for semiconductors and available on the market in a well polished and washed state, exhibiting higher surface smoothness and cleanness than the quarts glass substrate. Moreover, the silicon wafer substrate exhibits conductivity so that there is no necessity of a conductive film to be formed thereon in production of a stamper.

Figure 9B:
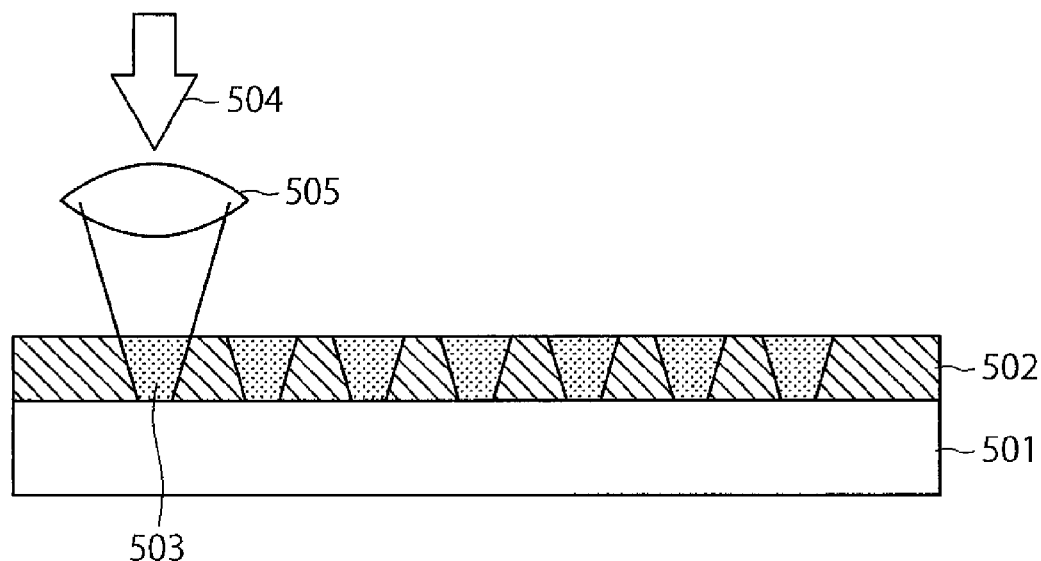
FIG. 9B is a sectional view schematically illustrating a method of producing the sample analysis disc according to the present invention.
Figure 20B:
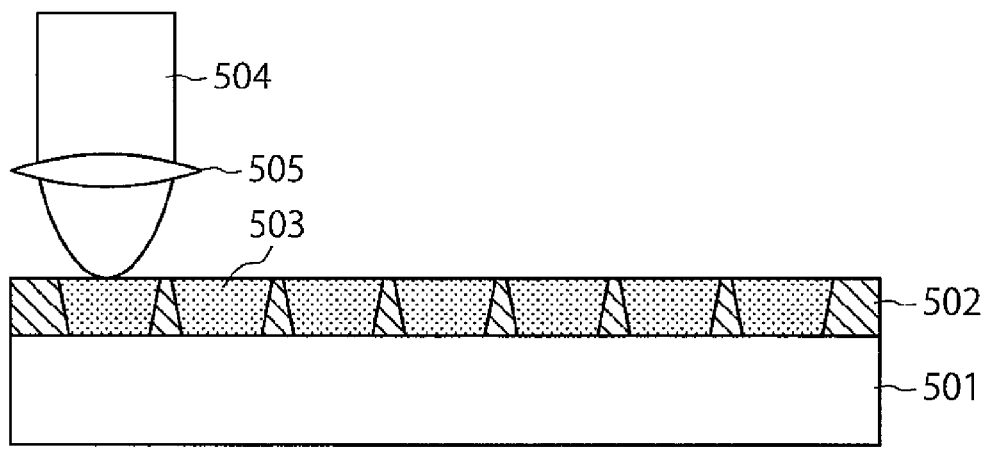
FIG. 20B is a sectional view schematically illustrating a method of producing the sample analysis disc according to the present invention.

Next, as shown in FIGS. 9B and 20B, the inorganic resist film 502 formed on the substrate 501 is exposed to a laser beam 504 that is converted into a spot beam through an objective lens 505, based on input information signals. Through the exposure, a latent image pattern 503 is formed on the inorganic resist film 502. It is preferable for the laser beam 504 used in this exposure to have a wavelength of about 400 nm, usually used for DVDs or the like. Moreover, it is preferable for the objective lens 505 used in this exposure to have a numerical aperture NA of about 0.9.

Figure 9C:
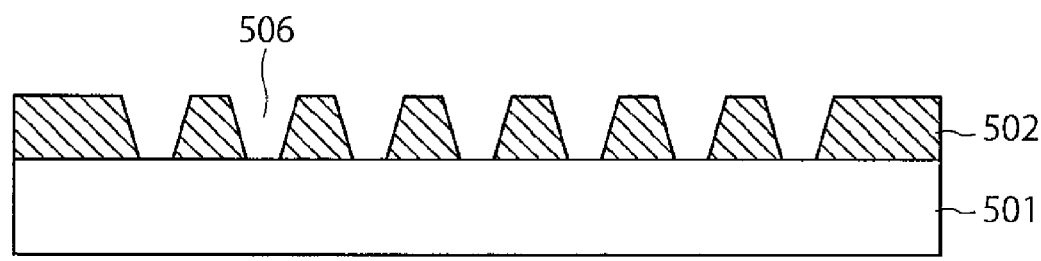
FIG. 9C is a sectional view schematically illustrating a method of producing the sample analysis disc according to the present invention.
Figure 20C:
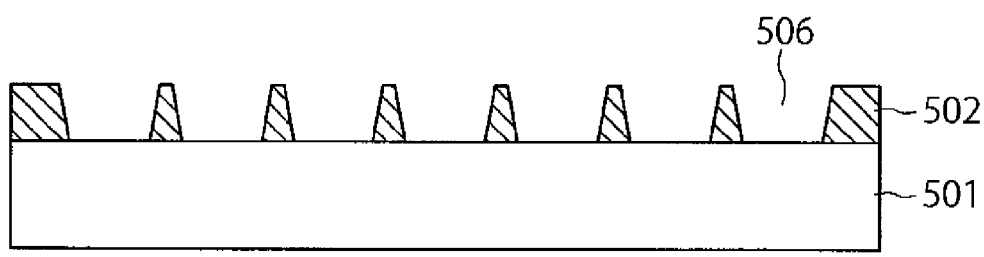
FIG. 20C is a sectional view schematically illustrating a method of producing the sample analysis disc according to the present invention.

Next, as shown in FIGS. 9C and 20C, the latent image pattern 503 formed on the inorganic resist film 502 of the substrate 501 is developed to form a resist pattern 506 (not shown for brevity), using a developing solution mostly an alkaline developing solution.

A material used for the inorganic resist film 502 in this embodiment is tungsten (W) oxide that exhibits high sensitivity to a laser beam of a wavelength to be used for exposure. One type of tungsten oxide is $WO_2$ that is stable at room temperature but turned into $WO_3$ when heated. Sputtered $WO_2$ having an amorphous structure is turned into $WO_3$ having a crystal structure when exposed to a laser beam for heating, thus becoming soluble in an alkaline solution.

Figure 9D:
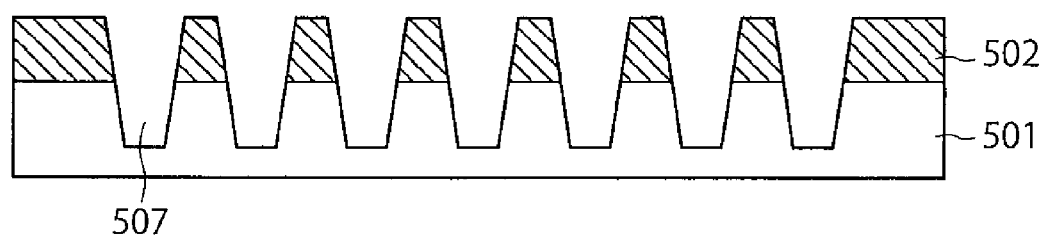
FIG. 9D is a sectional view schematically illustrating a method of producing the sample analysis disc according to the present invention.
Figure 20D:
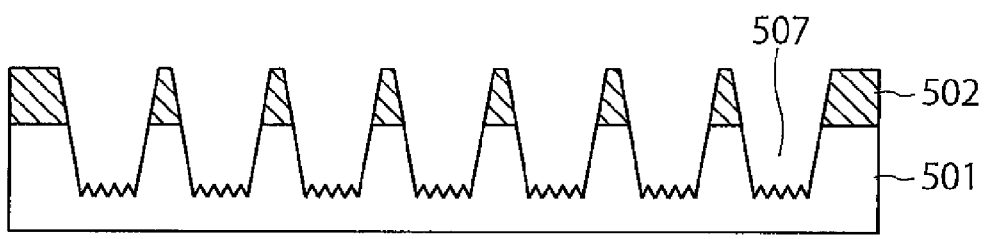
FIG. 20D is a sectional view schematically illustrating a method of producing the sample analysis disc according to the present invention.

Next, as shown in FIGS. 9D and 20D, the exposed portion of the substrate 501 is dry-etched through the resist pattern 506 as a mask, to directly form an etched pattern 507 (not shown for brevity). A fluorocarbon etching gas, such as a $CF_4$ gas, a $CHF_3$ gas, a $C_3F_8$ gas or a $C_4F_8$ gas exhibits a high etching rate of the substrate 501 to the resist pattern 506, thus achieving high etching selectivity. Especially, a $CHF_3$ etching gas achieves anisotropic etching with a higher etching rate in the vertical direction than in the transversal direction in FIGS. 9D and 20D, when the substrate 501 is made of quarts glass. The anisotropic etching gives the etched pattern 507 an almost rectangular shape in the cross section in the radius direction of the disc substrate 501 made of quarts glass, which allows the concave and convex sections to have a side face roughly perpendicular to the bottom surface of the disc substrate 501, as shown in FIGS. 9D and 20D. Moreover, the anisotropic etching allows the concave and convex sections (120 and 121 in FIG. 3A) to have deep grooves, the depth being controllable in accordance with etching conditions, which is conventionally determined by the thickness of a resist film.

Addition of a small amount of a hydrogen gas to the fluorocarbon etching gas increases the amount of radical polymers in etching, thus allowing different surface roughness between the concave sections 120 and convex sections 121. In this regard, a $CHF_3$ gas is used as the fluorocarbon etching gas in FIG. 9D. On the other hand, a gas mixture of a $CHF_3$ gas and a hydrogen gas is used as the fluorocarbon etching gas in FIG. 20D to give high surface roughness to the etched pattern 507 with higher hydrophilicity to the concave sections 120 than the convex sections 121. Moreover, with the use of the gas mixture mentioned above, the surface roughness can be controlled so that the concave and convex sections 120 and 121 have a surface roughness to be hydrophilic and water repellant, respectively, or the concave and convex sections 120 and 121 have a surface roughness to be water repellant and hydrophilic, respectively. The labeled beads can be immobilized only to the concave sections 120 or the convex sections 121 having a surface roughness to be hydrophilic.

The surface roughness depends on the amount of a hydrogen gas added in the etching step. The surface roughness in the range from about 10 nm to 20 nm gives appropriate hydrophilicity. On the other hand, high surface roughness of 30 nm or above gives adverse effects to the measurement accuracy due to increased noise in tracking and detection signals.

Figure 9E:
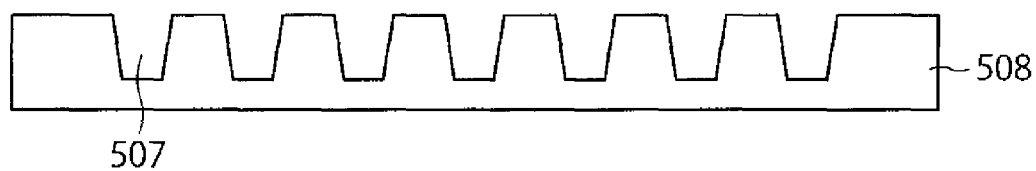
FIG. 9E is a sectional view schematically illustrating a method of producing the sample analysis disc according to the present invention.
Figure 20E:
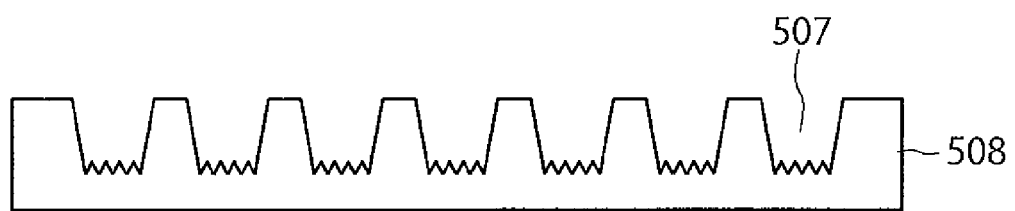
FIG. 20E is a sectional view schematically illustrating a method of producing the sample analysis disc according to the present invention.

Next, as shown in FIGS. 9E and 20E, isotropic ashing and trimming are performed with an applied voltage under an atmosphere of a fluorocarbon gas to remove the resist pattern 506 (FIGS. 9C and 20C although not shown for brevity) and reduce the surface roughness, thus producing a master disc 508 having the etched pattern 507 based on input information signals. A gas used as the fluorocarbon gas in the isotropic ashing and trimming steps is, for example, a $CF_4$ gas, a $CHF_3$ gas, a $C_3F_8$ gas or a $C_4F_8$ gas. Among them, the $CF_4$ gas is suitable for isotropic etching and hence the most appropriate as an etching gas.

Figure 9F:
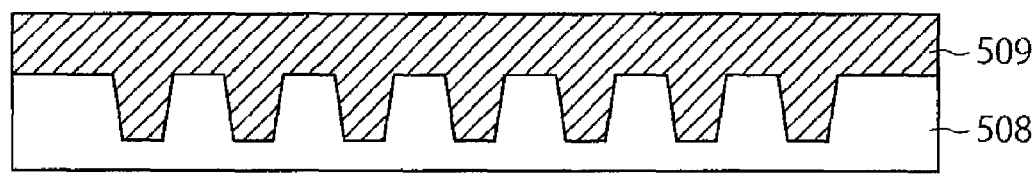
FIG. 9F is a sectional view schematically illustrating a method of producing the sample analysis disc according to the present invention.
Figure 20F:
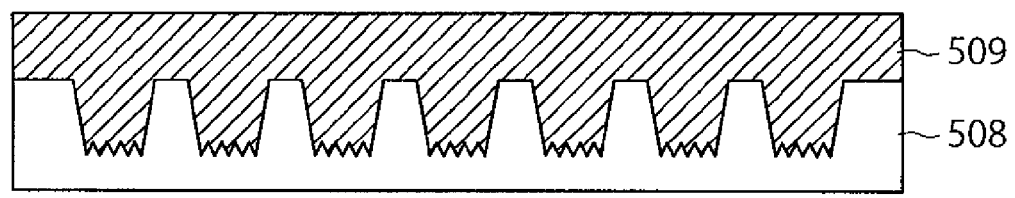
FIG. 20F is a sectional view schematically illustrating a method of producing the sample analysis disc according to the present invention.

Next, as shown in FIGS. 9F and 20F, sputtering is performed to the surface of the master disc 508 having the concave and convex sections to form a Ni film having a thickness in the range from about 50 nm to 200 nm. Electroforming is then applied to the Ni film to form a Ni plated film having a thickness in the range from about 100 μm to 500 μm. The Ni plated film is the imprinted version of the etched pattern 507 of the master disc 508, hence becoming a disc stamper 509 having concave and convex sections. The concave and convex sections of the disc stamper 509 are the inverted versions of the concave and convex sections of the etched pattern 507 of the master disc 508.

Figure 9G:
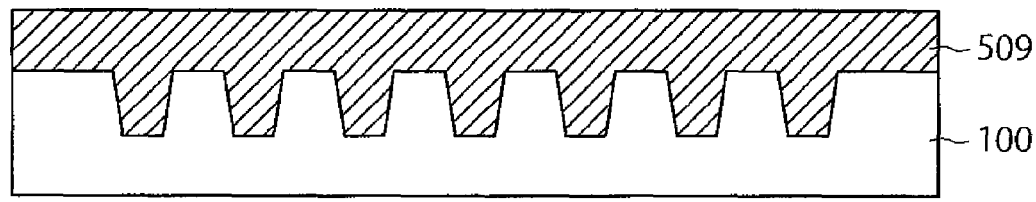
FIG. 9G is a sectional view schematically illustrating a method of producing the sample analysis disc according to the present invention.
Figure 20G:
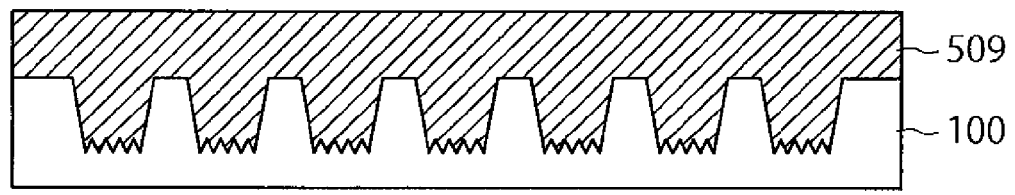
FIG. 20G is a sectional view schematically illustrating a method of producing the sample analysis disc according to the present invention.

Next, as shown in FIGS. 9G and 20G, the disc stamper 509 having the concave and convex sections is installed in an injection molding machine (not shown). Injection molding is performed to produce a sample analysis disc 100 having concave and convex sections with grooves 107 or pits 109 arranged spirally from the inner to the outer periphery or from the outer to the inner periphery, based on input information signals. The injection molding can be repeated to produce a large number of sample analysis discs 100.

Discussed next are experimental results of sample analysis using exemplary sample analysis discs 100 of the present invention produced by the production method described above according to the present invention.

The explanation starts with the production of exemplary sample analysis discs 100 with reference again to the FIGS. 9A to 9G and 20A to 20G.

Firstly, as shown in FIGS. 9A and 20A, a disc substrate 501 made of quarts glass was prepared with optical polishing and washing, followed by drying for a sufficient time. The disc substrate 501 was installed in a magnetron sputtering machine (not shown) with a target of a tungsten (W). Then, reactive sputtering was performed to the disc substrate 501 with 44-sccm argon and 6-sccm oxygen flow to form an inorganic resist film 502, thereon, having an amorphous structure with a film thickness of 50 nm.

Next, as shown in FIGS. 9B and 20B, the disc substrate 501 made of quarts glass and having the amorphous inorganic resist film 502 thereon was installed in a uniaxial-rotary exposure system equipped with a 405-nm wavelength semiconductor laser (not shown) and an objective lens 505 having a numerical aperture NA of 0.9. The amorphous inorganic resist film 502 formed on the substrate 501 was exposed to a laser beam 504 at a linear velocity of 5.0 m/s, to have a latent image pattern 503 having a land-groove pattern of grooves 107 and lands 108 at the same track pitch of 320 nm. Through the exposure, the areas of the amorphous inorganic resist film 502 corresponding to the latent image pattern 503 were changed into a crystalline state. The latent image pattern 503 can be formed for pits, a randomly modulated signal, etc., other than a land-groove pattern, under control of an emission pattern of the laser beam 504.

Next, as shown in FIGS. 9C and 20C, the substrate 501 made of quarts glass having the latent image pattern 503 was developed by being soaked into a developing solution of tetramethylammonium hydroxide (TMAH) at a concentration of 2.38 wt/% for 20 minutes. Through the development, the latent image pattern 503 was removed and a resist pattern 506 (not shown for brevity) was formed instead.

Next, as shown in FIGS. 9D and 20D, the exposed portion of the substrate 501 was dry-etched through the resist pattern 506 as a mask. In detail, the dry etching was performed with: a $CHF_3$ gas only in FIG. 9D; and a gas mixture of a $CHF_3$ gas and a hydrogen gas at a mixture ratio of 0.1 for the hydrogen gas to the gas mixture, in FIG. 20D. Moreover, dry etching was performed with an applied power of 100 watts for six minutes under a 4-pa atmosphere for higher anisotropy to form a line-and-space etched pattern 507 with a depth of 140 nm and a full width half maximum of 220 nm for grooves.

Next, as shown in FIGS. 9E and 20E, $CF_4$-gas ashing was performed to the etched pattern 507 formed on the substrate 501, with an applied voltage of 70 watts under a 15-pa atmosphere of $CF_4$ and $O_2$ at a mixture ratio of 5:2. Through the ashing, the resist pattern 506 (FIGS. 9C and 20C although not shown for brevity) was removed and the surface roughness was reduced, thus a master disc 508 having the etched pattern 507 was produced.

Next, as shown in FIGS. 9F and 20F, sputtering was performed to form a Ni film having a thickness of 150 nm on the master disc 508, followed by electroforming, to form a Ni plated film having a thickness of 300 μnm. The Ni plated film is the imprinted version of the etched pattern 507 of the master disc 508, hence becoming a disc stamper 509 having concave and convex sections.

Next, as shown in FIGS. 9G and 20G, the disc stamper 509 having the concave and convex sections was installed in an injection molding machine (not shown) to produce exemplary sample analysis discs 100 having grooves 107 and lands 108 arranged spirally from the inner to the outer periphery. The exemplary sample analysis discs 100 had a thickness of 1.1 mm, a track pitch of 320 mm, a depth of 140 nm, and a full width half maximum of 220 nm for the grooves 107. Especially, the exemplary sample analysis disc 100 produced as shown in FIG. 20G had surface roughness of about 16 nm and about 3 nm for the grooves 107 and lands 108, respectively, when measured by an atomic force microscope (AFM).

After the exemplary sample analysis discs 100 were produced as described above, antibodies 210 for use in specific interaction with sample antigens 200 were immobilized to the track area 105 (FIG. 2) of the exemplary discs 100. In detail, the antibodies 210 were immobilized to the grooves 107 and lands 108, and also the surrounding zones in the track area 105.

When the exemplary sample analysis discs 100 are formed with pits 109, instead of the grooves 107 and lands 108, the antibodies 210 are immobilized to the pits 109 and the surrounding zones in the track area 105. Moreover, the antibodies 210 may be immobilized in the grooves 107 only or the pits 109 only.

In detail, in the experiments, biotin (as the antibody 210) was dropped on the exemplary sample analysis discs 100 with a pipette at a volume of 10 μL. Then, biotin was bound to the surface of each of labeled beads 110 having a diameter of 140 nm and contained in a solution at a concentration of 100 μg/mL, so that each labeled bead 110 was modified with biotin. Next, a solvent modified with avidin for use in specific interaction with biodin was dropped, with a pipette at a volume of 1 μL, on the area of the exemplary sample analysis discs 100 where biotin had been dropped at a volume of 10 μL, to have sandwich antigen-antibody interaction. After the interaction, unreacted labeled beads 110 were washed away from the exemplary sample analysis discs 100, followed by disc surface drying.

Each exemplary sample analysis disc 100 having the sandwich antigen-antibody interaction occurred as described above was installed in the reading apparatus 1 as shown in FIG. 1. The exemplary sample analysis disc 100 was rotated at a constant linear velocity of 4.92 m/s. While the exemplary sample analysis disc 100 was being rotated, a laser beam having a wavelength of 405 nm was emitted from the laser oscillator 6 at a power of 0.35 mW and focused onto the disc surface through the objective lens 3 having a numerical aperture (NA) of 0.85. A return beam from the disc surface was received by the quad photodiode of the photodetector 9. Each signal component of a quad sum signal from the quad photodiode was sent to the controller 10 in order to observe the quad sum signal while tracking the spiral grooves 107.

In the experiments, a Shibasoku LM330 DVD tester was modified for observation of the quad sum signal. The number of reacted labeled beads 110 was counted by a Yokogawa TA720 time interval analyzer for 100 tracks of each exemplary sample analysis disc 100. The count number of the reacted labeled beads 110 was 45685 for 100 tracks of the exemplary sample analysis disc 100 produced as explained with reference to FIGS. 9A to 9G.

Figure 10:
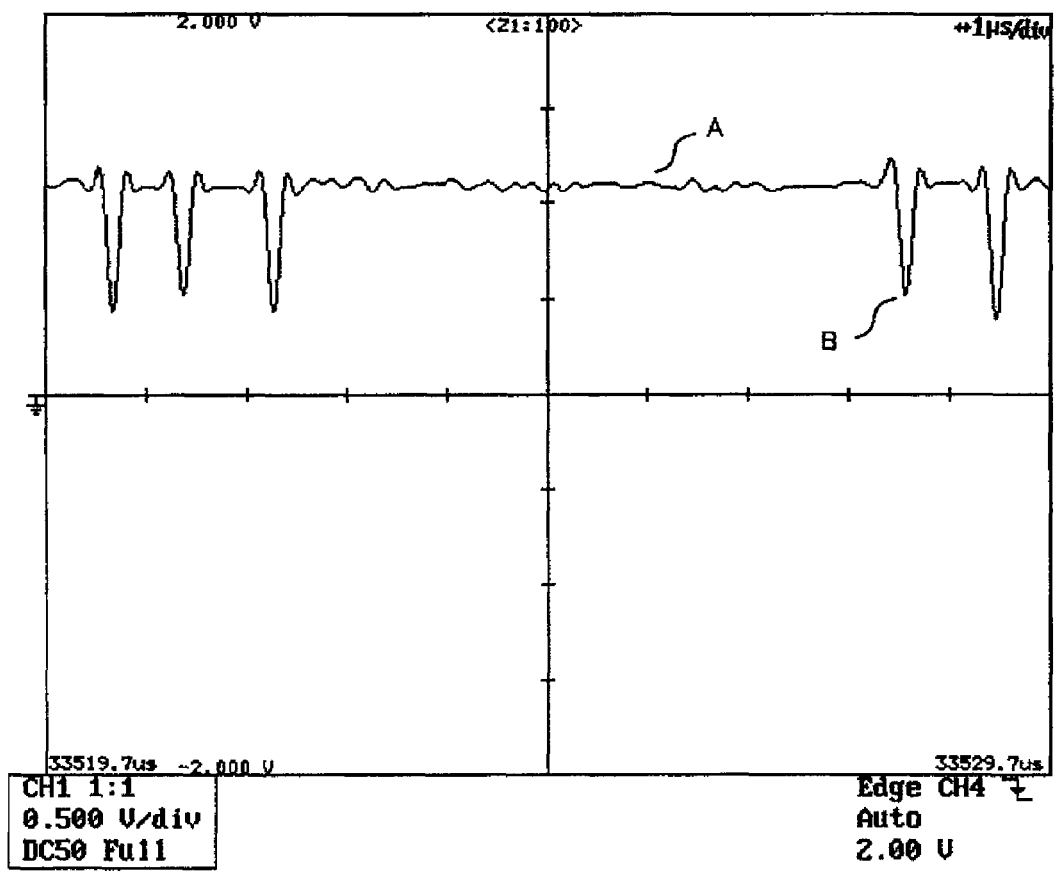
FIG. 10 is a view showing signal waveforms detected from labeled beads immobilized to the sample analysis disc according to the present invention.

A portion of a signal observed by a Yokogawa DL7440 digital oscilloscope is shown in FIG. 10. In FIG. 10, a relatively flat signal waveform A indicates that no labeled bead 110 was detected whereas a signal waveform B having a much lower signal voltage level indicates that a labeled bead 110 was detected. It is clearly shown in FIG. 10 that signal components each corresponding to one reacted labeled bead 110 have a much lower signal voltage level than the other signal components not corresponding to reacted labeled beads 110. A result of frequency analysis of each signal component corresponding to one reacted labeled bead 110 agreed with the diameter of each labeled bead 110 that was 140 nm.

The accuracy of the count number of the reacted labeled beads 110 was examined through reaction in a solvent of low to high concentration. For the examination, the labeled beads 110 were modified with biotin at each bead surface. Moreover, solvents modified with avidin for use in specific interaction with biodin were prepared at different concentrations by being adjusted to have concentration of 100 times (×100), 10 times (×10), 1 time (×1), 1/10 times (×1/10), 1/100 times (×1/100), and 1/1000 times (×1/1000).

Using the labeled beads 110 modified with biotin and the solvents modified with avidin and adjusted to have the different concentrations, the number of reacted labeled beads 110 was counted in the same way as explained above. A result of counting is shown in FIG. 21 for the exemplary sample analysis disc 100 produced as explained with reference to FIGS. 9A to 9G. It is understood from FIG. 21 that the number of reacted labeled beads 110 for 100 tracks of the exemplary sample analysis disc 100 was proportional to the concentration of the solvent from high (×100) to low (×1/1000). Moreover, the number of reacted labeled beads 110 at the concentration of 1 time (×1) in FIG. 21 is 45688 that is almost equal to 45685 counted in the experiments explained above, indicating high reproducibility of counting of the number of reacted labeled beads 110.

The accuracy of counting of the number of reacted is discussed further with some comparative examples.

In a first comparative example, labeled beads 110 were adjusted to have 300 nm in diameter larger than the width of the grooves 107 of the exemplary sample analysis disc 100 produced as explained with reference to FIGS. 9A to 9G. The counting of the number of reacted labeled beads 110 was carried out in the same way as the experiments explained above. A result of the counting showed that the labeled beads 110 having the large diameter caused increase in crosstalk components to adjacent tracks to make difficult stable tracking, resulting in counting impossible.

Figure 11:
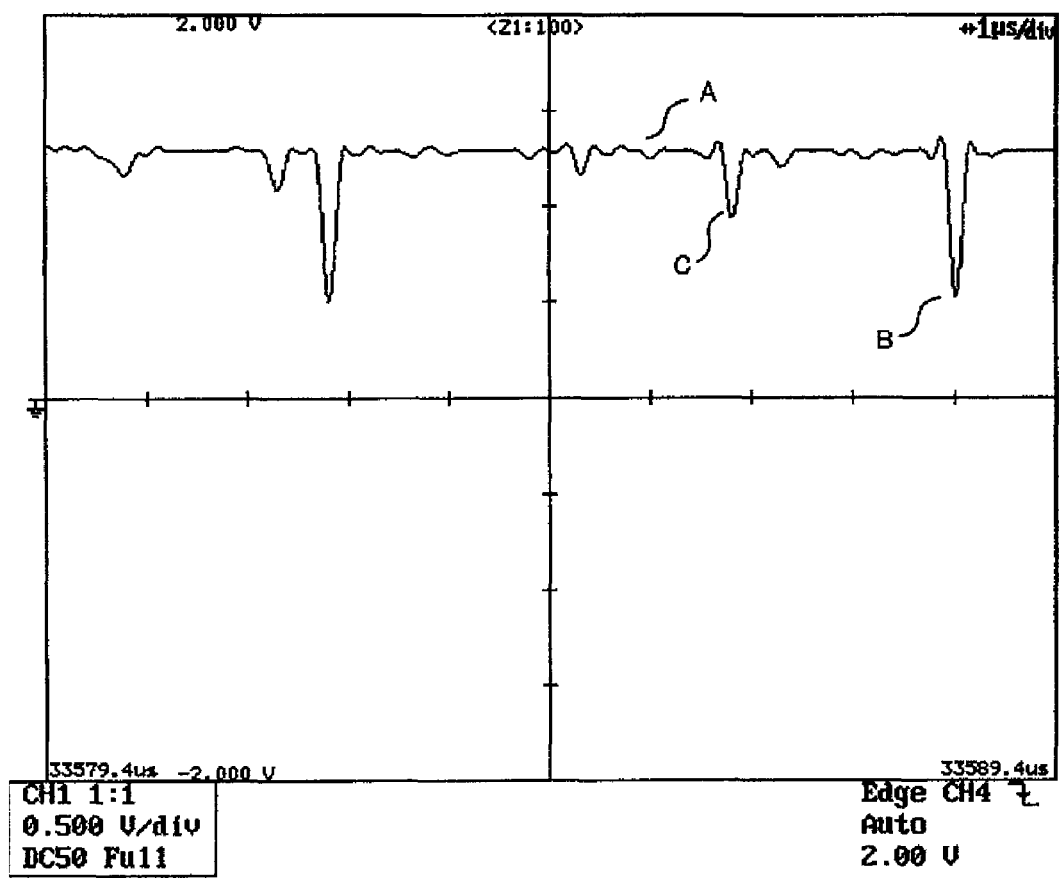
FIG. 11 is a view showing signal waveforms detected from labeled beads immobilized to the sample analysis disc according to the present invention, for comparison.

In a second comparative example, labeled beads 110 were adjusted to have 100 nm in diameter smaller than the width of the grooves 107 of the exemplary sample analysis disc 100 produced as explained with reference to FIGS. 9A to 9G. The counting of the number of reacted labeled beads 110 was carried out in the same way as the experiments explained above. The counting was successful with stable tracking signals, as shown in FIG. 22. A portion of a signal observed by a Yokogawa DL7440 digital oscilloscope is shown in FIG. 11. In signal waveforms shown in FIG. 11, a relatively flat signal waveform A indicates that no labeled bead 110 was detected whereas a signal waveform B having a much lower signal voltage level indicates that a reacted labeled bead 110 was detected. Also observed in FIG. 11 is a signal waveform C having a comparatively low signal voltage level but not distinguishable from the relatively flat signal waveform A, due to the immobilization of a plurality of labeled beads 110 to the grooves 107, the immobilization of labeled beads 110 displaced from the center of the grooves 107, etc. It is understood from FIG. 22 that the number of reacted labeled beads 110 for 100 tracks of the exemplary sample analysis disc 100 produced as explained with reference to FIGS. 9A to 9G was not proportional to the concentration of the solvent from high (×100) to low (×1/1000), with low accuracy.

Concerning the result shown in FIG. 11, immobilization of labeled beads displaced from the center of grooves tends to occur when a sample analysis disc is produced according to the DVD or Blu-Ray disc standards. In detail, the land and groove width is about 370 nm and about 160 nm for DVD and Blu-Ray discs, respectively. Compared to these land and groove widths, the diameter of antibodies is mostly several ten nanometers. Therefore, it is not always happened that antibodies are immobilized to the center of lands or grooves. The immobilization displaced from the center of lands or grooves could cause erroneous detection. For example, it could happen that, even though a beam scans a labeled bead immobilized to a groove, a labeled bead detected through the scanning is not the one immobilized to the groove, but a labeled bead bound to an antibody immobilized to an adjacent land, especially, to a land area on the groove side. If this happens, there is a big error in counting the number of antigens to be assayed.

In a third comparative example, a comparative sample analysis disc 100 was produced having almost the same surface roughness for grooves 107 and lands 108, with a $CHF_3$ etching gas in the master disc production process. In detail, the comparative sample analysis disc 100 was produced having the same size as the exemplary sample analysis discs 100, with a thickness of 1.1 mm, a track pitch of 320 mm, a depth of 140 nm, and a full width half maximum of 220 nm for the grooves 107. Moreover, the surface roughness of the comparative sample analysis disc 100 was about 4 nm and about 3 nm for the grooves 107 and lands 108, respectively, when measured by an atomic force microscope (AFM).

Counting of the number of reacted labeled beads 110 was carried out in the same way as the experiments explained above, using the comparative sample analysis disc 100 of the third comparative example. Although not shown, like the second comparative example (FIG. 11), the observed signal in the third comparative example contained a signal waveform C having a comparatively low signal voltage level but not distinguishable from a relatively flat signal waveform A. Moreover, almost the same surface roughness of about 4 nm and about 3 nm for the grooves 107 and lands 108, respectively, caused increase in crosstalk components from adjacent grooves 107 and lands 108 to make difficult stable tracking. Furthermore, almost the same surface roughness of the grooves 107 and lands 108 made undistinguishable between the signal level indicating no existence of labeled beads 110 and the signal level indicating labeled beads 110 immobilized on the lands 108. A result of counting the number of reacted labeled beads 110 in the third comparative example is shown in FIG. 23. When compared to the result of counting shown in FIG. 21 using the exemplary sample analysis disc 100 produced as explained with reference to FIGS. 9A to 9G, FIG. 23 shows count numbers roughly half of those in FIG. 21, inaccurate at high (×100) to low (×1/1000) solvent concentration.

Described next with respect to FIGS. 12 to 15 are modifications to the sample analysis disc 100 according to the present invention, concerning reflectance (light reflectance) of grooves 107 (FIG. 3A) or pits 109 (FIG. 3B), the configuration of the modifications basically the same as that shown in FIGS. 1 to 4.

Labeled beads 110 to be used for the modifications to the sample analysis disc 100 are adjusted to have a smaller diameter than a beam spot 115 (FIGS. 12 and 14) focused on to the detection zone 104 (FIG. 2) through the objective lens 3 of the reading apparatus 1 (FIG. 1). A smaller diameter of the labeled beads 110 allows signal detection through diffraction on the labeled beads 110. Moreover, the labeled beads 110 to be used for the modifications to the sample analysis disc 100 are adjusted to have a higher reflectance than the substrate of the modifications to the sample analysis disc 100. A higher reflectance of the labeled beads 110 enhances diffracted beam components from the labeled beads 110. This results in enhancement of the interference on the pupil of the objective lens 3, which further enhances amplification of signals from the labeled beads 110.

A high reflectance can be given to the labeled beads 110 by covering each labeled bead 110 with: a layer of a high refractive index or a film of a high reflectance index; or a resin with a specific substance as the core of the bead 110, the substance exhibiting a higher reflectance index than the resin. Moreover, a high reflectance can be given to the labeled beads 110 by producing the beads 110 with a resin mixed with substances that exhibit different refractive indices.

Like reproduction of data from ordinary optical discs, in the modifications, the interference between diffracted beams from the grooves 107 or pits 109 and diffracted beams from other sections of the disc is used to detect signals having large magnitude for detection of labeled beads 110. In the detection based on the interference, a phase difference between a laser beam emitted from the laser oscillator 6 (FIG. 1) and diffracted from the labeled beads 110, and a reflected beam from the disc surface on which the labeled beads 110 have been immobilized is adjusted to have a wavelength that is half of the wavelength of the emitted laser beam. The half wavelength of the phase difference maximizes the magnitude of signals based on the difference in amount of reflected beams depending on whether labeled beads 110 are detected or not.

The phase of a laser beam diffracted from the labeled beads 110 depends on the size, material, etc. of the labeled beads 110 and also three-dimensional distribution of complex index of refraction of the labeled beads 110. For the detection of the labeled beads 110 in the air, it is preferable for the labeled beads 110 to have a diameter that is about 1/4 of the wavelength of an emitted laser beam. In detail, it is preferable for the labeled beads 110 to have a diameter that is about 100 nm and about 160 nm for a laser beam having a wavelength of 405 nm and 650 nm, respectively.

The labeled beads 110 adjusted to have a diameter in the range from about 100 nm to about 160 nm explained above allows stable detection when proteins are detected. This is because labeled beads 110 adjusted to have such a diameter have no extreme difference in size compared to proteins. On the other hand, if the labeled beads 110 are adjusted to have a large diameter such as several hundred nanometers or larger, it could happen that a labeled bead 110 is pealed from a captured protein due to its own weight.

The diameter in the range from about 100 nm to about 160 nm for the labeled beads 110 explained above is smaller than the diameter of a beam spot 115 (FIGS. 12 and 14) of a laser beam for reading the sample analysis disc (the modifications to the sample analysis disc 100). The diameter adjustment allows signal detection based on the interference between diffracted beams from the grooves 107 or pits 109 and diffracted beams from other sections of the disc. When the diameter of the beam spot 115 is defined as that of an airy disc, the spot diameter is 581 nm for a laser beam to be used for a Blu-ray disc, having a wavelength of 405 nm through an objective lens having a numerical aperture (NA) of 0.85 whereas 1300 nm for a laser beam to be used for a DVD, having a wavelength of 650 nm through an objective lens having a numerical aperture (NA) of 0.6.

The modifications, concerning the reflectance of grooves 107 (FIG. 3A) or pits 109 (FIG. 3B), to the sample analysis disc 100 according to the present invention, for signal detection using the labeled beads 110 for which the diameter is adjusted as explained above, will be described now in detail.

In a first modification, the grooves 107 or pits 109 are adjusted to exhibit a high reflectance when no labeled bead 110 exists in the grooves 107 or pits 109 whereas a low reflectance when labeled beads 110 exist therein. The high reflectance is set to be high enough whereas the low reflectance is set to be appropriately low so that the signal magnitude from labeled bead 110 becomes maximum. The low reflectance should not to be lowered to zero otherwise causing difficulty in focus and tracking servo. Such reflectances are achieved with adjustments to the depth of the grooves 107 or pits 109 to give zero or near n wavelength (n being an integer) to the phase of reflected and refracted beams from the grooves 107 or pits 109. It is preferable to have an appropriate phase difference between the refracted beams. This is because complete in-phase causes no generation of tracking signals. There are options for the depth of the grooves 107 or pits 109 due to cyclic phase change if the depth varies.

In a second modification, the grooves 107 pits 109 are adjusted to exhibit a low reflectance when no labeled bead 110 exists in the grooves 107 pits 109 whereas a high reflectance when labeled beads 110 exist therein. The low reflectance is set to be low enough whereas the high reflectance is set to be appropriately high so that the signal magnitude from labeled bead 110 becomes maximum. Such reflectances are achieved with adjustments to the depth of the grooves 107 or pits 109 to give 1/2 wavelength to the phase of reflected and refracted beams from the grooves 107 or pits 109. When labeled beads 110 exist in the grooves 107 or pits 109, refracted beams from the labeled beads 110 become near in-phase and the grooves 107 or pits 109 exhibit a high reflectance. Therefore, signals obtained from labeled beads 110 in the second modification are of opposite polarity of those obtained in the first modification.

The first or second modification with the labeled beads 110 adjusted to have a smaller diameter than the beam spot 115 (FIGS. 12 and 14) achieves maximum signal magnitude from the labeled bead 110. The labeled beads 110 adjusted to have a smaller diameter than the beam spot 115 is, however, affected by lowered spatial frequency characteristics of the reading apparatus 1, thus giving smaller signal magnitude. The smaller signal magnitude is caused by decrease in refracted beam components from the labeled beads 110. In order to solve this problem, the labeled beads 110 are adjusted to have a higher reflectance than the substrate of the modifications to the sample analysis disc 100 to have larger signal magnitude, as described above.

Figure 12:
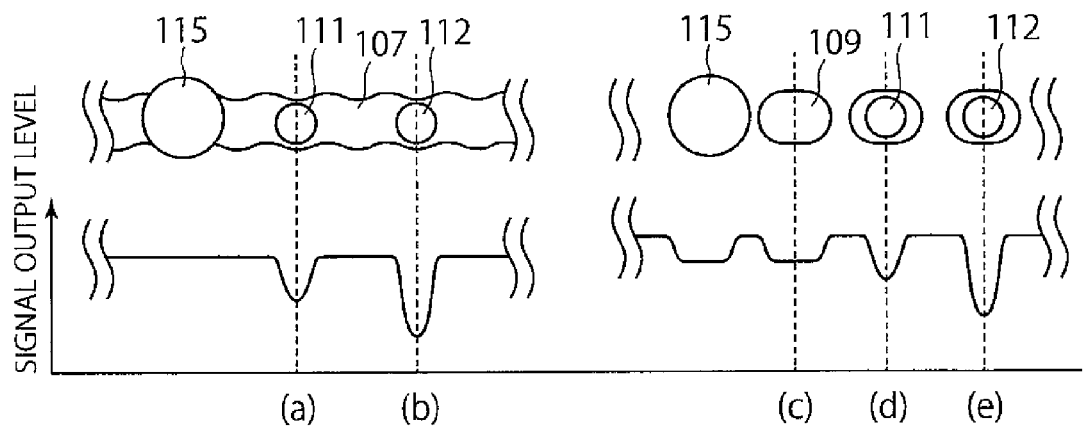
FIG. 12 is a view schematically illustrating scanning of grooves or pits in a modification to the sample analysis disc according to the present invention, with schematic illustration of signal waveforms detected from labeled beads.

FIG. 12 illustrates the first modification in which the grooves 107 or pits 109 are adjusted to exhibit a high reflectance when no labeled bead 110 exists in the grooves 107 or pits 109 whereas a low reflectance when labeled beads 110 exist therein. In detail, the high reflectance is set to be high enough whereas the low reflectance is set to be appropriately low so that the signal magnitude from labeled bead 110 becomes maximum, as described above. Illustrated in the left side of FIG. 12 is signal detection through a reflected beam by tracing with the beam spot 115, with a low-reflectance bead 111 and a high-reflectance bead 112 immobilized in a groove 107, as the labeled beads 110. Illustrated in the right side of FIG. 12 is signal detection through a reflected beam by tracing with the beam spot 115, with a low-reflectance bead 111 and a high-reflectance bead 112 immobilized in pits 109, as the labeled beads 110.

In the case of the first modification shown in FIG. 12, the labeled beads 110 adjusted to have, for example, 140 nm in diameter and 2/1 wavelength in phase for a reflected beam are immobilized in the grooves 107 or pits 109, for use in reproduction by the reading apparatus 1 with the optical constant compatible with a Blu-ray disc. In this case, the track pitch is adjusted to have 320 nm the same as a Blu-ray disc and the grooves 107 or pits 109 are adjusted to have 20 nm in depth. The adjustments give a concave shape to the grooves 107 or pits 109 when viewed from the reading apparatus side. Then, the labeled beads 110 are immobilized in the grooves 107 or pits 109 but not completely filled in the grooves 107 or pits 109 due to the larger diameter of the labeled beads 110 than the depth of the grooves 107 or pits 109.

Also schematically shown in FIG. 12 is a signal waveform detected from the labeled beads 110. The labeled beads 110 (the low- and high-reflectance beads 111 and 112) immobilized in the grooves 107 (or the land 108 not shown) or the pits 109 cause refracted beams in a reverse phase to reduce a signal output level, as indicated by waveforms (a), (b), (d) and (e). However, the high-reflectance beads 112 that exhibit a higher reflectance than the low-reflectance beads 111 give a high rate of change in signal output, as indicated by the waveforms (b) and (e).

Figure 13:
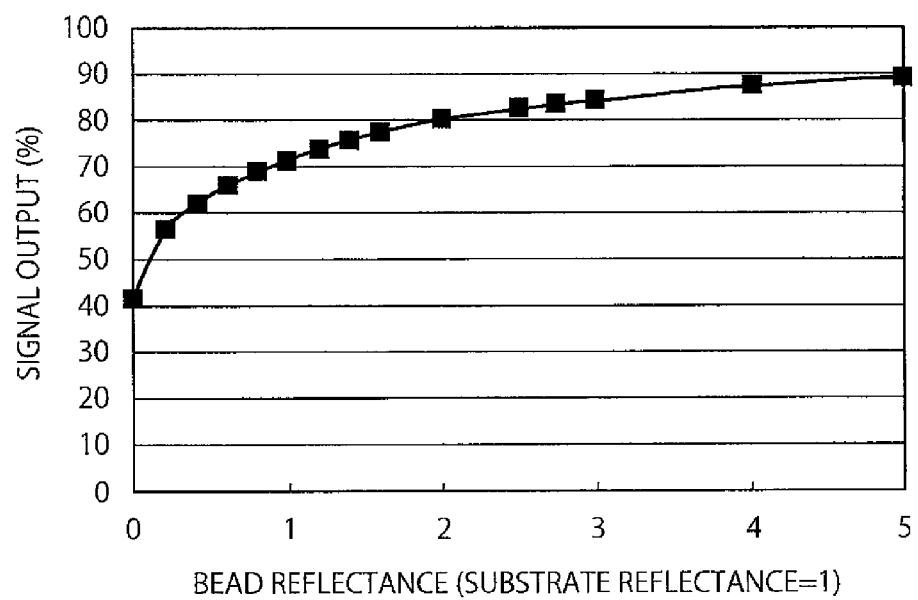
FIG. 13 shows a result of analysis of the rate of change in signal output depending on the reflectance of labeled beads, obtained based on scalar analysis, in relation to FIG. 12.

FIG. 13 shows a result of analysis of the rate of change in signal output depending on the reflectance of labeled beads 110, obtained based on scalar analysis. Although data is not shown, similar characteristics was confirmed by experiments. It is understood from FIG. 13 that a higher reflectance of the labeled beads 110 enhances refracted beams in a reverse phase which enhances output signal magnitude.

Figure 14:
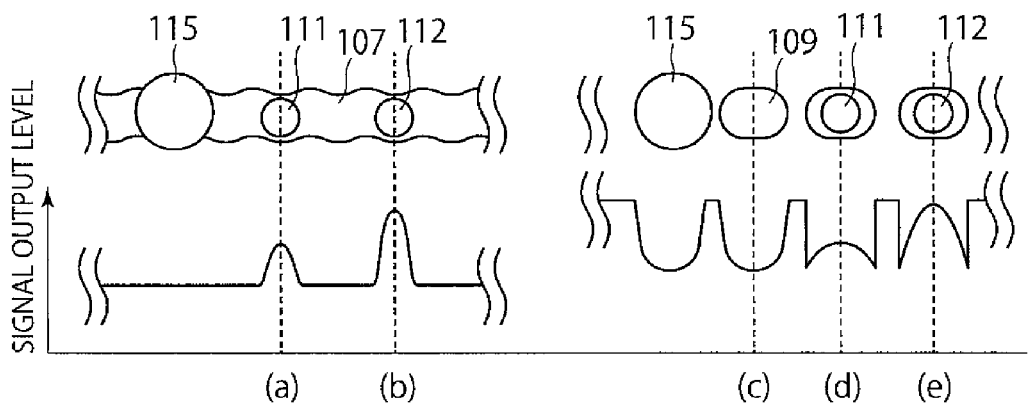
FIG. 14 is a view schematically illustrating scanning of grooves or pits in a modification to the sample analysis disc according to the present invention, with schematic illustration of signal waveforms detected from labeled beads.

FIG. 14 illustrates the second modification in which the grooves 107 or pits 109 are adjusted to exhibit a low reflectance when no labeled bead 110 exists in the grooves 107 pits 109 whereas a high reflectance when labeled beads 110 exist therein. In detail, the low reflectance is set to be low enough whereas the high reflectance is set to be appropriately high so that the signal magnitude from labeled bead 110 becomes maximum, as described above. Illustrated in the left side of FIG. 14 is signal detection through a reflected beam with tracing with the beam spot 115, with a low-reflectance bead 111 and a high-reflectance bead 112 immobilized in a groove 107, as the labeled beads 110. Illustrated in the right side of FIG. 14 is signal detection through a reflected beam by tracing with the beam spot 115, with a low-reflectance bead 111 and a high-reflectance bead 112 immobilized in pits 109, as the labeled beads 110.

In the case of the second modification shown in FIG. 14, the labeled beads 110 adjusted to have, for example, 140 nm in diameter are immobilized in the grooves 107 or pits 109, for use in reproduction by the reading apparatus 1 with the optical constant compatible with a Blu-ray disc. In this case, the track pitch is adjusted to have 320 nm the same as a Blu-ray disc and the grooves 107 or pits 109 are adjusted to have 120 nm in depth. The adjustments give a concave shape to the grooves 107 or pits 109 when viewed from the reading apparatus side. Then, the labeled beads 110 are immobilized in the grooves 107 or pits 109 but not completely filled in the grooves 107 or pits 109 due to the larger diameter of the labeled beads 110 than the depth of the grooves 107 or pits 109.

Also schematically shown in FIG. 14 is a signal waveform detected from the labeled beads 110. The labeled beads 110 (the low- and high-reflectance beads 111 and 112) immobilized in the grooves 107 (or the land 108 not shown) or the pits 109 cause increase in reflectance to increase a signal output level, as indicated by waveforms (a), (b), (d) and (e). Moreover, the high-reflectance beads 112 that exhibit a higher reflectance than the low-reflectance beads 111 give a high rate of change in signal output, as indicated by the waveforms (b) and (e).

Figure 15:
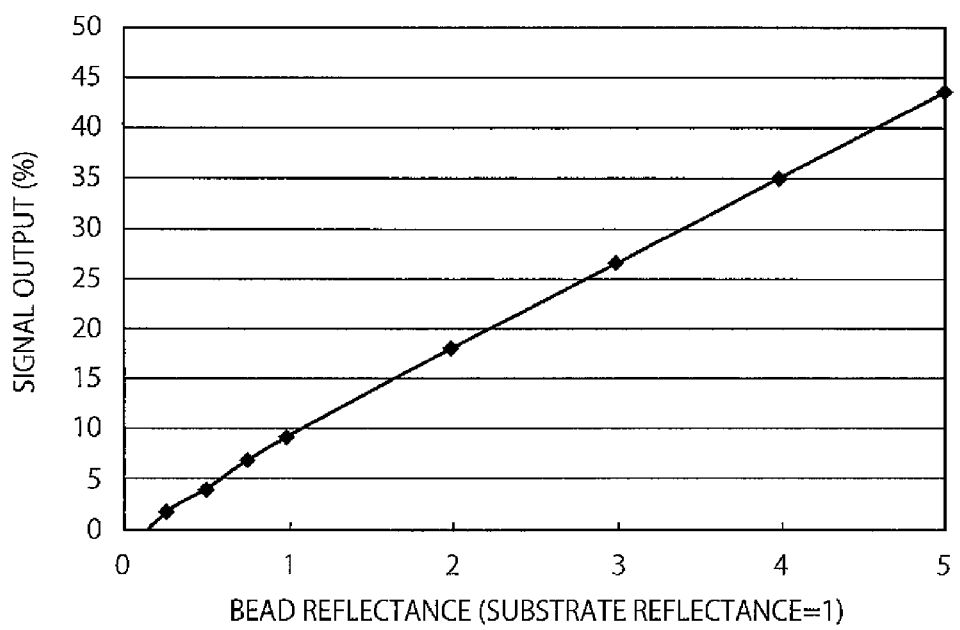
FIG. 15 shows a result of analysis of the rate of change in signal output depending on the reflectance of labeled beads, obtained based on scalar analysis, in relation to FIG. 14.

FIG. 15 shows a result of analysis of the rate of change in signal output depending on the reflectance of labeled beads 110, obtained based on scalar analysis. Although data is not shown, similar characteristics was confirmed by experiments. It is understood from FIG. 15 that a higher reflectance of the labeled beads 110 enhances output signal magnitude.

It is also preferable for the labeled beads 110 to have a diameter smaller than the width of the grooves 107 or pits 109 but not so small so that not two or more but only one labeled bead 110 can be captured by and immobilized in each groove 107 or pit 109. This diameter adjustment achieves signal detection at high S/N by tracking the grooves 107 or pits 109 with restricted change in signal magnitude and detection error.

Next, a method of immobilizing capture antibodies 211 only in the grooves 107 of the sample analysis disc 100 according to the present invention will be described with reference to FIGS. 16A to 19.

Figure 16A:
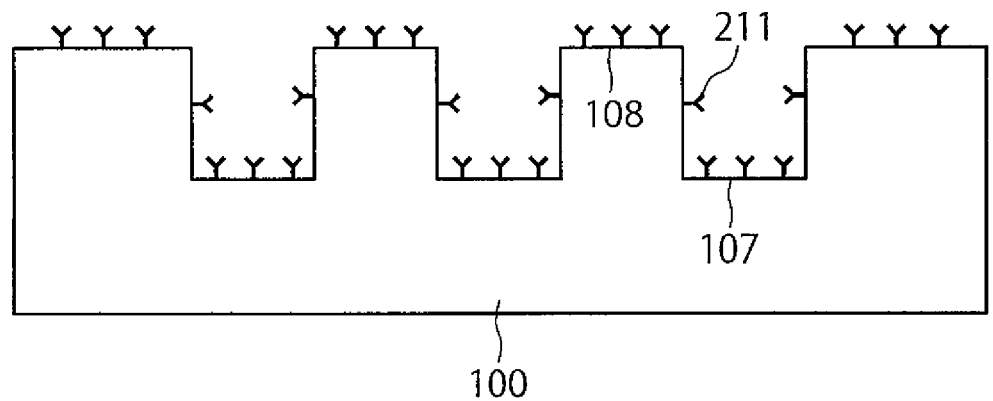
FIG. 16A is a sectional view schematically illustrating a method of immobilizing capture antibodies to the sample analysis disc according to the present invention.

As shown in FIG. 16A, capture antibodies 211 to be immobilized to the track area 105 (FIG. 2) of the sample analysis disc 100 are immobilized to both of the grooves 107 and lands 108. Illustrated FIG. 16A is that the capture antibodies 211 are immobilized to the bottom and sidewall of each groove 107 and also each land 108. This immobilization is performed by: dispersing capture antibodies 211 in a buffer solution with a pH value adjusted to be suitable for capture antibodies to be immobilized; dropping or applying the buffer solution with the dispersed capture antibodies 211 in or on the substrate of the sample analysis disc 100 so that the capture antibodies 211 are spread on one portion of or over the substrate surface; and leaving the sample analysis disc 100 for a specific time at an appropriate temperature so that capture antibodies 211 can be physically stuck to or chemically bound to the disc surface.

Although not limited to, suitable materials for the substrate of the sample analysis disc 100 are polycarbonate resin and alicylic amorphous polyolefin resin, appropriate for injection molding for ordinary optical discs. It is also preferable to form a thin film of a substance that exhibits high wettability or a substance that has affinity with or can be bound to the capture antibody 211 on the surface of the grooves 107 and lands 108 made of such resin so that dropped or applied capture antibodies 211 can be easily immobilized to the grooves 107 and lands 108. However, care must be taken so that the thin film does not disfigure the grooves 107 and lands 108.

Figure 16B:
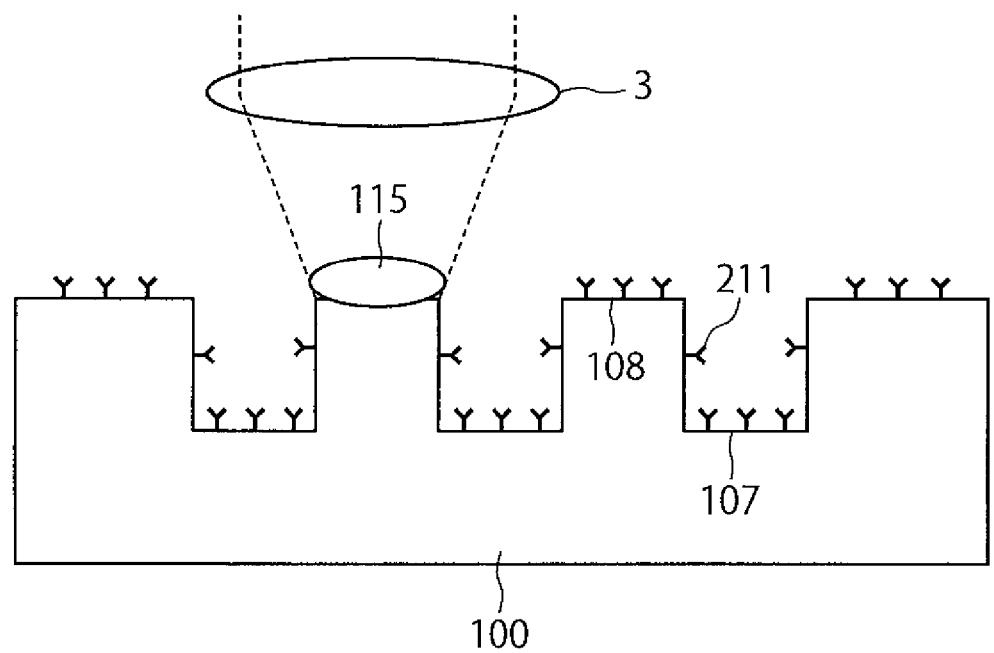
FIG. 16B is a sectional view schematically illustrating a method of immobilizing capture antibodies to the sample analysis disc according to the present invention.
Figure 17:
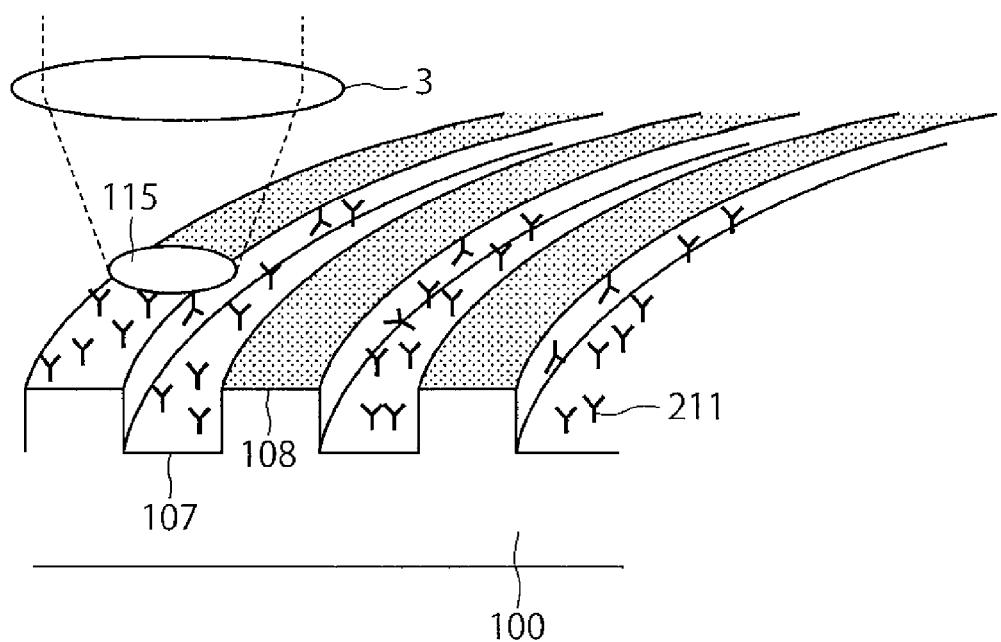
FIG. 17 a perspective view schematically illustrating a method of immobilizing capture antibodies to the sample analysis disc according to the present invention.
Figure 18:
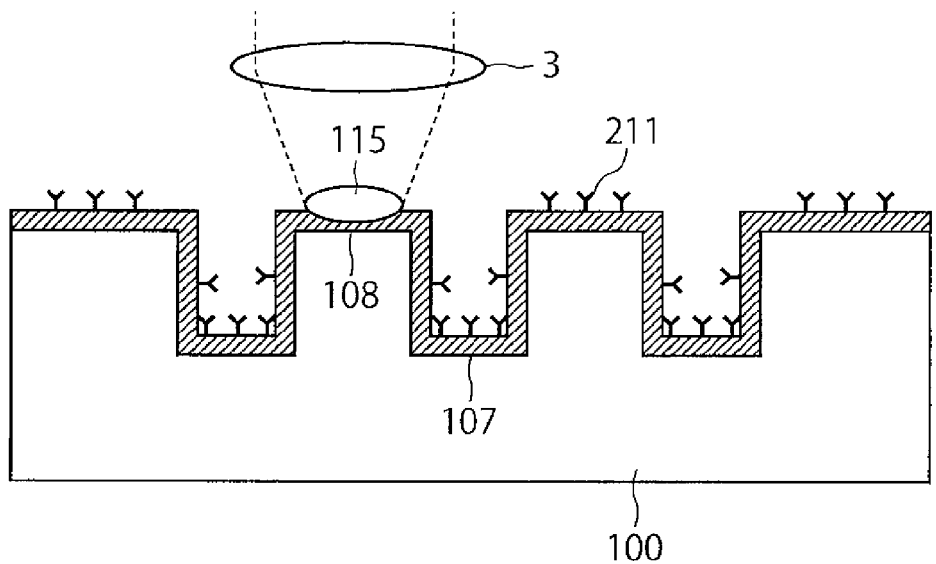
FIG. 18 is a sectional view schematically illustrating a method of immobilizing capture antibodies to the sample analysis disc according to the present invention.

Then, the sample analysis disc 100 having the capture antibodies 211 immobilized to the grooves 107 and lands 108 is installed in an optical-disc recording and reproducing apparatus. While the sample analysis disc 100 is being rotated, a focused laser beam is irradiated onto each land 108 continuously under control by focus and tracking servo, as shown in FIGS. 16B and 17. In detail, a focused laser beam at a laser power extremely larger than a laser power for ordinary reproduction (about 0.5 mW to 1 mW) is irradiated onto the land 108 to heat the land 108 at a high temperature by the thermal energy generated by the irradiated beam. The heating process decomposes or physically removes the capture antibodies 211 immobilized to the land 108, or at least denatures the capture antibodies 211 but not to the extent that specific interaction, such as antigen-antibody interaction, does not occur.

With continuous irradiation of the laser beam to the lands 108, the capture antibodies 211 immobilized to the lands 108 lose the function of a biochemical reaction, thus obtaining a sample analysis disc 100 having the capture antibodies 211 immobilized only to the grooves 107.

Although not limited to, a laser to be used in the heating process is preferably a near-infrared laser having a wavelength of 780 nm to 840 nm for efficiently decomposing the target capture antibodies 211, a red laser having a wavelength of 650 nm for DVDs, or a compact semiconductor laser such as a blue-violet laser having a wavelength of 405 nm for Blu-Ray discs.

When the capture antibodies 211 are made of a material that cannot be easily decomposed or denatured by the laser described above, a material that exhibits high absorption to the laser beam described above, for example, a dye (such as a cyanine dye) that exhibits high absorption at 780 nm, 650 nm or 405 nm, may be formed on the substrate surface of the sample analysis disc 100 having the grooves 107 and lands 108 formed thereon. Such a material can generate thermal energy when it absorbs a laser beam to decompose, denature or remove the capture antibodies 211.

Figure 19:
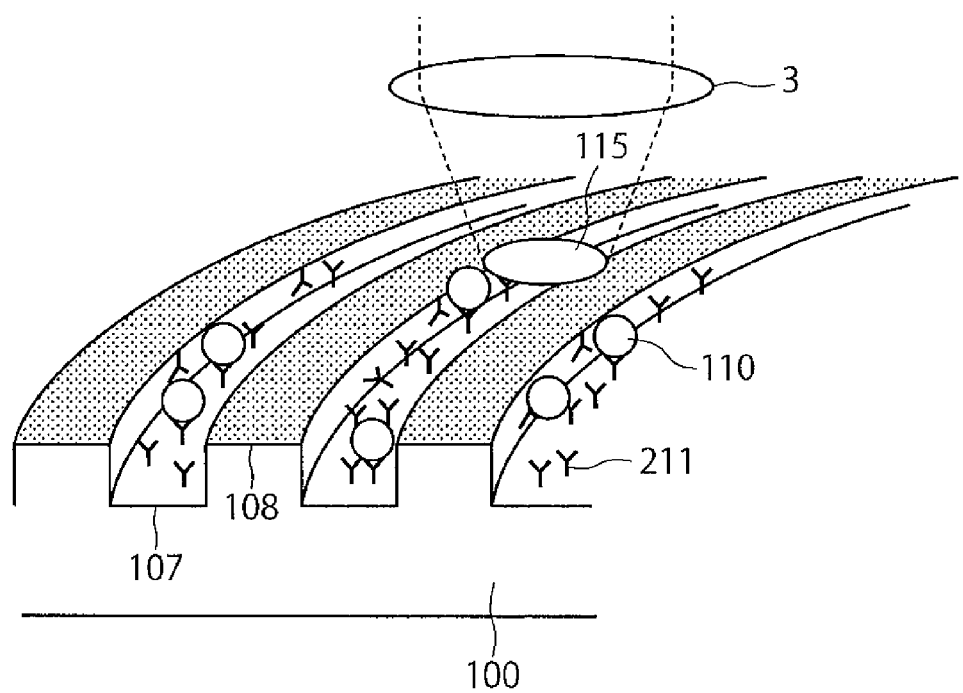
FIG. 19 is a perspective view schematically illustrating a method of immobilizing capture antibodies to the sample analysis disc according to the present invention.

With the method described above with respect to FIGS. 16A to 18, once the capture antibodies 211 are immobilized only to the grooves 107 and have antigen-antibody interaction, the labeled beads 110 for use in optical detection are located only in the grooves 107, as shown in FIG. 19. The sample analysis disc 100 having the labeled beads 110 only in the grooves 107 is then installed in the reading apparatus 1 (FIG. 1) for tracing the grooves 107 with tracking. The number of the labeled beads 110 only in the grooves 107 can be counted one by one at high speed with no double counting because of no labeled bead 110 on the lands 108 to move to the grooves 107. In this way, captured biopolymer (antigen 201 for assay) can be detected at high accuracy and high quantitativity for a sample at low to high concentration.

It is further understood by those skilled in the art that the foregoing description is a preferred embodiment of the disclosed apparatus or method and that various changes and modifications may be made in the invention without departing from the sprit and scope thereof.

For example, described above is the counting of labeled beads 110 to which immunological biopolymers of low to high concentration are bound due to the interaction of biotin and avidin. However, not only that, labeled bead counting can be performed with biopolymers of low to high concentration bound to labeled beads due to the interaction of, for example, hepatitis B antigens and the corresponding antibodies, depending on the type of biopolymers to be assayed.

Moreover, an antigen-antibody sandwich assay can be used in the present invention. Furthermore, counting of a plurality of types of labeled beads 110 can be simultaneously done with simultaneous interaction between a plurality of types of antigens and antibodies in separate areas of the disc substrate within the substrate area requirements.

Furthermore, it could happen that, due to insufficient immobilization of labeled beads 110 to the sample analysis disc 100, labeled beads 110 reacted with antigens 200 or antibodies 210 are washed away when the disc 100 is washed with pure water. This leads to difficulty in accurate assay proportional to the concentration. Such a problem would occur depending on the type of antigens 200, antibodies 210 and labeled beads 110, and also the surface roughness and wettability of the sample analysis disc 100. In order to avoid such a problem, the formation of a thin film on the sample analysis disc 100 or the surface treatment such as the application of a silane coupling agent, plasma treatment, etc. can be done before the antigen-antibody interaction on the disc surface under an appropriate condition.

Moreover, as shown in FIG. 3A, each concave section 120 (the groove 107) and the convex section 121 (the land 108) adjacent thereto share the side face 122. When the surface roughness adjustment is made for the concave and convex sections 120 and 121 as described with respect to FIG. 20D, the surface roughness of the side face 122 may be adjusted to the same as the concave section 120 or the convex section 121.

As disclosed above in detail, the present invention provides a sample analysis disc that can be used for sample analysis using optical pickups for use in ordinary optical discs, hence achieving sample analysis at low cost using a compact optical-disc reproducing apparatus. Moreover, the present invention provides a sample analysis disc by which the number of labeled beads can be counted one by one with no double counting at high speed and high accuracy. This counting allows accurate measurements of captured biopolymers (antigens) for a sample of low to high concentration.

What is claimed is:

1. A sample analysis disc comprising:
a disc surface;
a track area having concave sections and convex sections formed alternately on the disc surface; and
labeled beads immobilized to the track area, each labeled bead having a biopolymer bound thereto,
wherein only one of the labeled beads is allowed to be filled in each concave section, and
wherein a ratio of the diameter of each labeled bead to the width of each concave section is equal to or larger than 0.6, but smaller than 1, so that only one of the labeled beads is allowed to be filled in each concave section, and
a ratio of the width of each concave section to an interval between two adjacent concave sections in a direction of a radius of the sample analysis is equal to or larger than 0.65, wherein each concave section has a first edge section and an opposite second edge section in the direction of the radius, the first edge section being closer or farther than the second edge section to or from a center of the sample analysis disc in the direction of the radius, the interval being a distance between the first edge section of each concave section and the first edge section of a concave section next to each concave section in the direction of the radius.

2. The sample analysis disc according to claim 1, wherein each concave section is a groove or a pit.

3. The sample analysis disc according to claim 1, wherein each labeled bead has a diameter almost equal to or smaller than a width of each concave section.

4. The sample analysis disc according to claim 1, wherein each labeled bead exhibits a higher reflectance than the track area.

5. The sample analysis disc according to claim 1 further comprising:
   an outer section and an inner section that is closer than the outer section to a center of the sample analysis disc in a direction of a radius of the sample analysis disc;
   at least one inlet provided in the inner section, the inlet being for use in dropping of a sample including biopolymers in the sample analysis disc;
   a flow channel connected to the inlet in the inner section, the flow channel being used in reaction of the labeled beads with the biopolymers included in the sample; and
   a detection zone provided in the outer section and connected to the flow channel, wherein the concave sections are located in the detection zone, and the detection zone has a larger area than the flow channel.

6. The sample analysis disc according to claim 5, wherein the area of the detection zone becomes wider towards an outer periphery of the sample analysis disc.

7. The sample analysis disc according to claim 5, wherein different types of antigens are bound to the detection zone, depending on a distance from the center of the sample analysis disc.

8. The sample analysis disc according to claim 1, wherein the concave sections and the convex sections have different surface roughness.

9. The sample analysis disc according to claim 8, wherein the concave sections have a surface roughness to be hydrophilic and the convex sections have a surface roughness to be water repellant.

10. The sample analysis disc according to claim 9, wherein the labeled beads are immobilized only to the concave sections having a surface roughness to be hydrophilic.

11. The sample analysis disc according to claim 8, wherein the concave sections have a surface roughness to be water repellant and the convex sections have a surface roughness to be hydrophilic.

12. The sample analysis disc according to claim 11, wherein the labeled beads are immobilized only to the convex sections having a surface roughness to be hydrophilic.

13. A sample analysis disc comprising:
   a disc surface;
   a track area having concave sections and convex sections formed alternately on the disc surface; and
   labeled beads immobilized to the track area, each labeled bead having a biopolymer bound thereto,
   wherein a ratio of the diameter of each labeled bead to the width of each concave section is equal to or larger than 0.6, but smaller than 1, so that only one of the labeled beads is allowed to be filled in each concave section, and
   a ratio of the width of each concave section to an interval between two adjacent concave sections in a direction of a radius of the sample analysis is equal to or larger than 0.65, wherein each concave section has a first edge section and an opposite second edge section in the direction of the radius, the first edge section being closer or farther than the second edge section to or from a center of the sample analysis disc in the direction of the radius, the interval being a distance between the first edge section of each concave section and the first edge section of a concave section next to each concave section in the direction of the radius.

14. The sample analysis disc according to claim 13, wherein the concave sections and the convex sections have different surface roughness.

15. A sample analysis disc comprising:
   a disc surface;
   a track area having concave sections and convex sections formed alternately on the disc surface;
   labeled beads immobilized to the track area, each labeled bead having a biopolymer bound thereto, only one of the labeled beads being allowed to be filled in each concave section;
   an outer section and an inner section that is closer than the outer section to a center of the sample analysis disc in a direction of a radius of the sample analysis disc;
   at least one inlet provided in the inner section, the inlet being used in dropping of a sample including biopolymers in the sample analysis disc;
   a flow channel connected to the inlet in the inner section, the flow channel being used in reaction of the labeled beads with the biopolymers included in the sample; and
   a detection zone provided in the outer section and connected to the flow channel, wherein the concave sections are located in the detection zone, and the detection zone has a larger area than the flow channel,
   wherein a ratio of the diameter of each labeled bead to the width of each concave section is equal to or larger than 0.6, but smaller than 1, so that only one of the labeled beads is allowed to be filled in each concave section, and
   a ratio of the width of each concave section to an interval between two adjacent concave sections in a direction of a radius of the sample analysis is equal to or larger than 0.65, wherein each concave section has a first edge section and an opposite second edge section in the direction of the radius, the first edge section being closer or farther than the second edge section to or from a center of the sample analysis disc in the direction of the radius, the interval being a distance between the first edge section of each concave section and the first edge section of a concave section next to each concave section in the direction of the radius.

16. The sample analysis disc according to claim 15, wherein the concave sections and the convex sections have different surface roughness.

* * * * *